United States Patent [19]
Ohlmeyer

[11] Patent Number: 5,962,337
[45] Date of Patent: Oct. 5, 1999

[54] COMBINATORIAL 1,4-BENZODIAZEPIN-2,5-DIONE LIBRARY

[75] Inventor: Michael H. J. Ohlmeyer, Plainsboro, N.J.

[73] Assignee: Pharmacopeia, Inc., Princeton, N.J.

[21] Appl. No.: 08/996,579

[22] Filed: Dec. 23, 1997

Related U.S. Application Data

[63] Continuation-in-part of application No. PCT/US96/11070, Jun. 28, 1996.
[60] Provisional application No. 60/000,657, Jun. 29, 1995.
[51] Int. Cl.$^6$ ............... G01N 33/543; C07D 487/04; C07D 243/24
[52] U.S. Cl. ............ 436/518; 540/496; 540/506
[58] Field of Search ............ 436/518, 523–531; 540/496, 506

[56] References Cited

U.S. PATENT DOCUMENTS

| | | | |
|---|---|---|---|
| 3,624,073 | 11/1971 | Field et al. | 540/509 |
| 3,678,038 | 7/1972 | Field et al. | 540/504 |
| 4,554,272 | 11/1985 | Bock et al. | 514/219 |
| 5,428,157 | 6/1995 | Baldwin et al. | 540/509 |
| 5,438,055 | 8/1995 | Baldwin et al. | 514/221 |
| 5,556,969 | 9/1996 | Chambers et al. | 540/509 |
| 5,681,833 | 10/1997 | Piniero et al. | 514/215 |
| 5,696,110 | 12/1997 | Bourrain et al. | 514/211 |

OTHER PUBLICATIONS

Martin et al. J. Org. Chem, vol. 34, pp. 1359–1363, 1969.
Boojamra et al. J. Org. Chem, vol. 60, pp. 5742–5743, 1995.
Mayer et al. tetrahedron Lett., vol. 37, pp. 8081–8084, 1996.
Sugimori et al. Chem. Lett., vol. 9, pp. 869–870, 191997.
Sugimori et al. Tetrahedron, vol. 54, pp. 7997–8008, 1998.
Copp et al. J. Org. Chem., vol. 63, pp. 8024–8026, 1998.

*Primary Examiner*—Ponnathapura Achutamurthy
*Attorney, Agent, or Firm*—Heslin & Rothenberg, P.C.

[57] ABSTRACT

A method has now been found of synthesizing a combinatorial library of 1,4-benzodiazepin-2,5-diones on solid supports via an aza-Wittig ring closure, said compounds optionally encoded with tags, and to the use of this library in assays to discover biologically active compounds, and, optionally, to cleave 1,4-benzodiazepin-2,5-diones therefrom.

14 Claims, No Drawings

COMBINATORIAL 1,4-BENZODIAZEPIN-2,5-DIONE LIBRARY

CROSS REFERENCE

This application is a continuation-in-part of co-pending PCT application PCT/US96/11070, filed Jun. 28, 1996 which claims the benefit of provisional application Ser. No. 60/000,657, filed Jun. 29, 1995. The entire disclosures of the foregoing, as well as all patents and other references cited below are incorporated herein by reference.

BACKGROUND OF THE INVENTION

There is interest in methods for the synthesis of large numbers of diverse compounds which can be screened for various possible physiological or other activities. Techniques have been developed in which one adds individual units sequentially as part of the chemical synthesis to produce all or a substantial number of the possible compounds which can result from all the different choices possible at each sequential stage of the synthesis. See e.g., Still et al., PCT Appli. WO94/08051. For techniques such as these to be successful, numerous solid state chemical reactions must be developed.

Ellman et al., ("Progress Toward the Synthesis of a Library of 1,4-Benzodiazepin-2,5-diones" ACS National Meeting, Anaheim, Calif. Apr. 2–6, 1995, Abstr. ORGN264) have reported a solid-phase synthesis of 1,4 benzodiazepin-2,5-diones. The Ellman et al. method limits the diversity of the benzodiazepin-2,5-dione scaffold because attachment of the scaffold to the solid support during synthesis is through the benzene ring, a residuum remaining on said ring after detachment of the benzodiazepin-2,5-dione from the solid support. Solution-phase synthesis of 1,4 benzodiazepin-5-ones via intramolecular aza-Wittig reaction has been disclosed by Egushi et al. (SYNLETT, 295–6, April 1992).

It is also desirable for compounds produced by combinatorial synthesis to be amenable to methods by which one can determine the structure of the compounds so made. Brenner and Lerner (PNAS USA 81: 5381–83 (1992)) and WO 93/20242, for example, describe a synthesis wherein oligonucleotides are produced in parallel with and are chemically linked as genetic tags to oligopeptides as the compounds of interest. WO 93/06121 teaches methods for particles-based synthesis of random oligomers wherein identification tags on the particles are used to facilitate identification of the oligomer sequence synthesized. A detachable tagging system is described in Ohlmeyer et al., Proc. Natl. Acad. Sci. USA, 90, 10922–10926, December 1993.

SUMMARY OF THE INVENTION

The present invention relates to a method of synthesizing a combinatorial library of 1,4-benzodiazepin-5-ones on solid supports via an aza-Wittig ring closure, said compounds optionally encoded with tags, and to the use of this library in assays to discover biologically active compounds, and, optionally, to cleave 1,4-benzodiazepin-2,5-diones therefrom.

DETAILED DESCRIPTION OF THE INVENTION

The combinatorial chemical library which may be synthesized by the method of the present invention is represented by Formula I:

    I wherein:

Ⓢ is a solid support;

T'-L- is an identifier residue;

-L'-II' is a linker/ligand residue;

q is 0–30; and

II' is

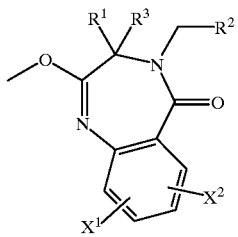    II' wherein:

$R^1$ is H, lower alkyl, c-lower alkyl, -or $(CH_2)_m R^4$, or $R^1$ and $R^2$, together with the atoms to which they are attached, join to form a 5-, or 6-membered heterocyclic ring, optionally monosubstituted with OH, alkoxy, or arylalkoxy;

$R^2$ is H, loweralkyl, aryl$R^6 R^7 R^8$, or heteroaryl$R^6 R^7 R^8$, or $R^1$ and $R^2$, together with the atoms to which they are attached, join to form a 5- or 6-membered heterocyclic ring, optionally monosubstituted with OH, alkoxy, or arylalkoxy;

$R^3$ is H or loweralkyl, $R^4$ is aryl, substituted aryl, heteroaryl, substituted heteroaryl, $NR^3 R^5$, $CO_2 R^3$, $CONR^3 R^3$, or OH;

$R^5$ is H, lower alkyl, —C(=NR$^3$)NHR$^3$, or —C(O)R$^3$;

$R^6, R^7$, and $R^8$ is each, independently, H, lower alkyl, lower alkoxy, halogen, aryl, lower alkylthio, X-aryl, X-substituted aryl, lower alkylaryl, C(hal)$_3$, $(CH_2)_m NR^3 R^5$, or —X—CH(CO$_2$R$^3$)$_2$, or $R^6$ and $R^7$, together with the atoms to which they are attached, join to form a 5- or 6-membered heterocyclic ring;

X is O or S; and $X^1$ and $X^2$ are independently chosen from hydrogen, loweralkyl, loweralkoxy, loweralkylthio, hydroxy, cyano, nitro, phenoxy, benzyloxy, halo, aryl, —NH(C=O)R$^3$ and carboxy, or $X^1$ and $X^2$ taken together represent a fused benzene ring substituted with hydrogen, loweralkyl, loweralkoxy, loweralkylthio, hydroxy, cyano, nitro, phenoxy, benzyloxy, halo, aryl, —NH(C=O)R$^3$; or carboxy.

Preferred libraries of Formula I are those Wherein T'-L- is of the formula III

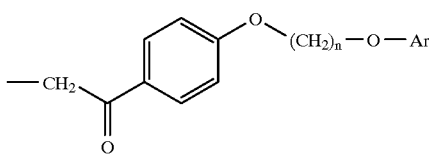    III wherein:

n=3–12;

Ar is halophenyl; and q is 3–12

More preferred libraries of Formula I are those wherein in Formula III: 1) n=3–12 and Ar is pentachlorophenyl; or 2) n=5–6 and Ar is 2,4,6-trichlorophenyl.

Depending on the choice of L' (see Table 1), the ligands of formula II may be detached by photolytic, oxidative, acidic, basic, or other cleavage techniques. For example, when -L'- is (a), acidic cleavage may be represented by:

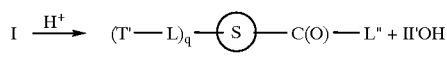

wherein L" is the residue from L' and II'OH is II, in its tautomeric amide form:

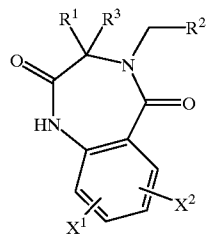

II wherein the symbols are as defined above for formula II'.

An embodiment of the invention is the solid phase synthesis of 1,4-benzodiazepin-2,5-diones via aza-Wittig ring closure. The process comprises:

a) attaching a set of suitably protected α-aminoacids or N-alkyl-α-aminoacids to solid supports to form resin linked N-alkyl-α-aminoacids; or b) attaching a set of suitably protected N-unsubstitued-α-aminoacids to solid supports to form resin linked N-unsubstitued-α-aminoacids and reductively alkylating said resin linked aminoacids with a set of aldehydes to form resin linked N-arylalkyl or heteroarylalkyl-α-aminoacids;

c) acylating the resin linked N-alkyl-α-aminoacids or the N-arylalkyl or heteroarylalkyl-α-aminoacids of steps (a) or (b) with a set of 2-azidobenzoyl chlorides to form resin linked N-(2-azidobenzoyl)amino esters;

d) cyclizing the resin linked N-(2-azidobenzoyl)amino esters of step (c) via aza-Wittig ring closure to form resin linked benzodiazepines; and, optionally, e) cleaving the resin linked benzodiazepines of step (d) to form 1,4-benzodiazepin-2,5-diones.

A preferred embodiment of the invention is the solid phase synthesis of 1,4-benzodiazepin-2,5-diones via aza-Wittig ring closure, wherein the process comprises:

a) reacting a set of suitably protected α-aminoacids of the formula:

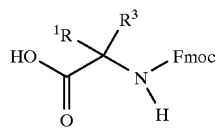

in the presence of DMF and DMAP with solid supports suspended in methylene chloride to form resin linked aminoacids of the formula:

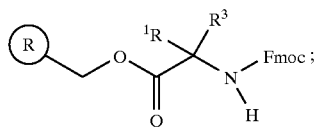

b) reacting the resin linked aminoacids of step (a), suspended in DMF and acetic acid, with a set of aldehydes of the formula HC(O)R² in HOAc/DMF and sodium cyanoborohydride in THF to form resin linked N-alkyl-α-aminoacids of the formula:

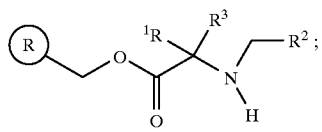

c) reacting the resin linked N-alkyl-α-aminoacids of step (b), in methylene chloride and diisopropylethylamine, with 2-azidobenzoyl chlorides of formula:

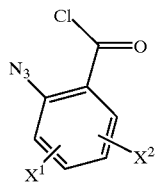

to form resin linked N-(2-azidobenzoyl)amino esters of formula:

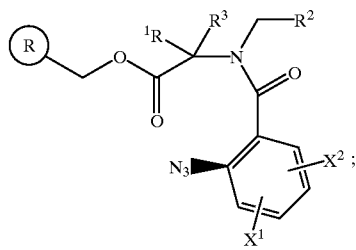

d) treating the resin linked N-(2-azidobenzoyl)amino esters of step (c), suspended in an involatile solvent (i.e., a non-protic, organic solvent with a boiling point of 80–140° C.) such as toluene, xylene, or chlorobenzene, with an excess of a trivalent phosphorus reagent such as triphenylphosphine or tributylphosphine at 80–150° C. and then cooling said mixture to room temperature to form resin linked benzodiazepines of formula:

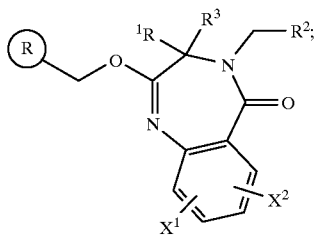

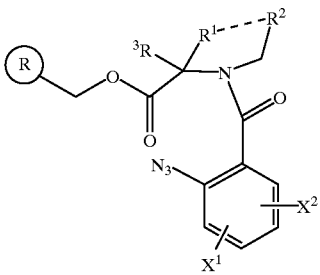

and, optionally, e) suspending the resin linked benzodiazepines of step (d) in TFA/water at room temperature for 1–24 hours to form 1,4-benzodiazepin-2,5-diones of formula:

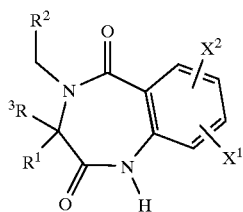

wherein the symbols are as defined above for formula II'.

A second preferred embodiment of the invention is the solid phase synthesis of 1,4-benzodiazepin-2,5-diones and 1,3-cyclo-1,4-benzodiazepin-2,5-diones via aza-Wittig ring closure, wherein the process comprises:

a) reacting a set of suitably protected α-aminoacids of the formula:

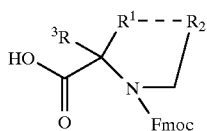

in the presence of DMF and DMAP with solid supports suspended in methylene chloride to form resin linked aminoacids of the formula:

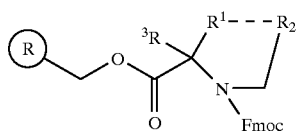

b) reacting the resin linked N-alkyl-α-aminoacids of step (b), in methylene chloride and diisopropylethylamine, with 2-azidobenzoyl chlorides of formula:

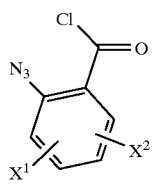

to form resin linked N-(2-azidobenzoyl)amino esters of formula:

c) treating the resin linked N-(2-azidobenzoyl)amino esters of step (b), suspended in an involatile solvent (i.e., a non-protic, organic solvent with a boiling point of 80–140° C.) such as toluene, xylene, or chlorobenzene, with an excess of a trivalent phosphorus reagent such as triphenylphosphine or tributylphosphine at 80–150° C. and then cooling said mixture to room temperature to form resin linked benzodiazepines of formula:

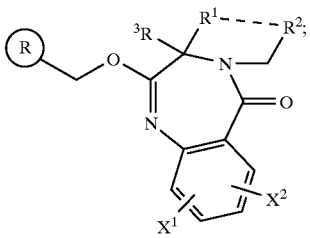

d) suspending the resin linked benzodiazepines of step (c) in TFA/water at room temperature for 1–24 hours to form 1,4-benzodiazepin-2,5-diones of formula:

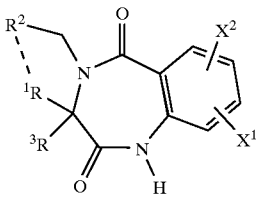

wherein the symbols are as defined above for formula II'.

Another embodiment of the invention is the use of the combinatorial library of Formula I in assays to discover biologically active compounds (ligands) of Formula II. Thus, an aspect of the invention is a method of identifying a compound having a desired characteristic which comprises synthesizing a combinatorial library of Formula I and testing the library of Formula I, either attached to the solid support or detached therefrom, in an assay which identifies compounds of Formula II having the desired characteristic. Another embodiment of the invention is a method of identifying a compound having a desired characteristic which comprises testing the library of Formula I, either attached to the solid support or detached therefrom, in an assay which identifies compounds of Formula II having the desired characteristic. A further embodiment of the invention is determining the structure of any compound so identified.

It is within the scope of the present invention that the determination of the structures of compounds having the desired characteristic can be accomplished by decoding the tags (represented by T'-L- in Formula I) or, alternatively, by deconvolution of the library (Smith et al., *BioMed. Chem. Lett.*, 4, 2821 (1994); Kurth et al., *J. Org. Chem.*, 59, 5862 (1994); Murphy et al., *J. Am. Chem. Soc.*, 117, 7029 (1995); Cambell et al., *J. Am. Chem. Soc.*, 117, 5381 (1995); and Erb et al., *Proc. Nat. Acad. Sci. USA*, 91, 11422 (1994)). In the latter case, q=0 and the library of the present invention may be represented by Formula I'

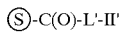 -C(O)-L'-II'    I' wherein the symbols are as defined for Formula I.

Another embodiment of the invention is the use of divinylbenzene-cross-linked, polyethyleneglycol-grafted polystyrene beads optionally functionalized with amino groups (for example, TENTAGEL® S $NH_2$, Rapp Polymere) as the solid supports for constructing a combinatorial library of Formula I or I'.

Definitions

The following abbreviations have the indicated meaning:
Bn=benzyl
BnOH=benzyl alcohol
Boc=t-butyloxycarbonyl
Bz=benzoyl
c-=cyclo
DEAD=diethylazodicarboxylate
DCM=dichloromethane=methylene chloride
DIC=diisopropylcarbodiimide
DMAP=4-N,N-dimethylaminopyridine
DMF=N,N-dimethylformamide
equiv.=equivalent
Et=ethyl
FACS=fluorescence activated cell sorting
Fmoc=9-fluorenylmethoxycarbonyl
Fmoc-OSu=9-fluorenylmethylsuccinimidyl carbonate
GC=gas chromatography
hr=hour, hours
m-=meta
Me=methyl
p-=para
PEG=polyethylene glycol
Ph=phenyl
r.t.=room temperature
sat'd=saturated
s-=secondary
t-=tertiary
t-Boc=t-butyloxycarbonyl
TFA=trifluoroacetic acid
THF=tetrahydrofuran
Thy=thienyl
TsOH=p-toluenesulfonic acid Alkyl is intended to include linear, branched, or cyclic hydrocarbon structures and combinations thereof. "Lower alkyl" means alkyl groups of from 1 to 8 carbon atoms. Examples of lower alkyl groups include methyl, ethyl, propyl, isopropyl, butyl, s- and t-butyl, pentyl, hexyl, octyl, cyclopropylethyl, and the like. "Lower cycloalkyl" includes cycloalkyl groups of from 3 to 8 carbon atoms. Examples of lower cycloalkyl groups include c-propyl, c-butyl, c-pentyl, 2-methylcyclopropyl, cyclopropylmethyl, norbornyl, and the like.

"Alkenyl" is $C_2$–$C_8$ alkenyl of a linear, branched, or cyclic ($C_5$–$C_6$) configuration and combinations thereof. Examples of alkenyl groups include vinyl, allyl, isopropenyl, pentenyl, hexenyl, c-hexenyl, 1-propenyl, 2-butenyl, 2-methyl-2-butenyl, and the like.

"Alkynyl" is $C_2$–$C_8$ alkynyl of a linear or branched configuration and combinations thereof. Examples of alk-enyl groups include ethyne, propyne, butyne, pentyne, 3-methyl-1-butyne, 3,3-dimethyl-1-butyne, and the like.

"Alkoxy" means alkoxy groups of from 1 to 8 carbon atoms of a straight, branched, or cyclic configuration and combinations thereof. Examples of alkoxy groups include methoxy, ethoxy, propoxy, isopropoxy, cyclopropyloxy, cyclohexyloxy, and the like.

"Acylamino" means acylamino groups of from 1 to 8 carbon atoms of a straight, branched or cyclic configuration and combinations thereof. Examples of acylamino groups are acetylamino, butylamino, cyclohexylamino, and the like.

Hal means halogen, which includes F, Cl, Br, and I.

"Halophenyl" means phenyl substituted by 1–5 halogen atoms. Halophenyl includes pentachlorophenyl, pentafluorophenyl, and 2,4,6-trichlorophenyl.

"Aryl" and "heteroaryl" mean a 5- or 6-membered aromatic or heteroaromatic ring containing 0–3 heteroatoms selected from O, N, and S; a bicyclic 9- or 10-membered aromatic or heteroaromatic ring system containing 0–3 heteroatoms selected from O, N, and S; or a tricyclic 13- or 14-membered aromatic or heteroaromatic ring system containing 0–3 heteroatoms selected from O, N, and S; each of which rings is optionally substituted with 1–3 substituents selected from lower alkyl, alkenyl, alkynyl, substituted lower alkyl, substituted alkenyl, substituted alkynyl, =O, $NO_2$, halogen, hydroxy, alkoxy, cyano, $NR^3R^3$, acylamino, phenyl, benzyl, phenoxy, benzyloxy, heteroaryl, and heteroaryloxy, each of said phenyl, benzyl, phenoxy, benzyloxy, heteroaryl, and heteroaryloxy is optionally substituted with 1–3 substituents selected from lower alkyl, alkenyl, alkynyl, halogen, hydroxy, alkoxy, $C(hal)_3$, cyano, phenyl, phenoxy, benzyl, benzyloxy, caboxamido, heteroaryl, heteroaryloxy, $NO_2$, and $NR^3R^3$;

The aromatic 6- to 14-membered carbocyclic rings include benzene, naphthalene, indane, tetralin, and fluorene and the 5- to 10-membered aromatic heterocyclic rings include imidazole, pyridine, indole, thiophene, benzopyranone, thiazole, furan, benzimidazole, quinoline, isoquinoline, quinoxaline, pyrimidine, pyrazine, tetrazole, and pyrazole.

"Substituted" alkyl, alkenyl, or alkynyl means alkyl, alkenyl, or alkynyl wherein up to three H atoms on each C therein are replaced by halogen, hydroxy, loweralkoxy, carboxy, carboalkoxy, carboxamido, cyano, carbonyl, $NO_2$, $NR^3R^3$, alkylthio, sulfoxide, sulfone, acylamino, amidino, phenyl, benzyl, heteroaryl, phenoxy, benzyloxy, heteroaryloxy, and substituted phenyl, benzyl, heteroaryl, phenoxy, benzyloxy, and heteroaryloxy.

It is intended that the definitions of any substituent or symbol (e.g., $R^3$, m, etc.) in a particular molecule be independent of its definitions elsewhere in the molecule. Thus, "$NR^3R^3$" represents NHH, $NHCH_3$, $N(CH_3)_2$, etc.

The linkers may be any component capable of being selectively cleaved to release both T and II from the solid support. See, e.g., Greene and Wuts, "Protective Groups in Organic Synthesis", 2nd ed., Wiley, 1991. Specific linkers L' are depicted in Table 1 (note that -L-=—C(O)L'- or —$CH_2$—C(O)L'-), which also shows cleavage reagents. In designing a synthetic scheme, L and L' are chosen such that they are orthogonally reactive, i.e., they must allow for removal of either T or II (where T=T'-OH) without removal of the other since simultaneous cleavage of both T and II from the solid support is disadvantageous. In the structures as shown, the left-hand bond is the point of attachment to the solid support (via —C(O)— for L' and —C(O)— or —$CH_2C$(O)— for L) and the right-hand bond is the point of attachment to either T or II.

The tags of this invention, T, are chemical entities which possess several properties: they must be detachable from the solid supports, preferably by photolysis or oxidation; they must be individually differentiable, and preferably separable; they must be stable under the synthetic conditions; they must be capable of being detected at very low concentrations, e.g., $10^{-18}$ to $10^{-9}$ mole; they should be identifiable with readily-available equipment which does not require sophisticated technical capabilities to operate; and they should be relatively economical. The tags may be structurally related or unrelated, e.g., a homologous series, repetitive functional groups, related members of the Periodic Chart, different isotopes, combinations thereof, and the like. At the end of the combinatorial synthesis, to each solid support, there will usually be attached at least 0.01 femtomol, usually 0.001–50 pmol, of each tag. The tags may be aliphatic, alicyclic, aromatic, heterocyclic, or combinations thereof. Distinguishing features may be the number of repetitive units, such as methylene groups in an alkyl moiety; alkyleneoxy groups in a polyalkyleneoxy moiety; halo groups in a polyhalo compound; α- and/or β-substituted ethylene groups where the substituents may be alkyl groups, oxy, carboxy, amino, halo, or the like; isotopes; etc.

The materials upon which the combinatorial syntheses of the invention are performed are referred to as solid supports, beads, and resins. These terms are intended to include:

a) beads, pellets, disks, fibers, gels, or particles such as cellulose beads, pore-glass beads, silica gels, polystyrene beads optionally cross-linked with divinylbenzene and optionally grafted with polyethylene glycol and optionally functionalized with amino, hydroxy, carboxy, or halo groups, grafted co-poly beads, polyacrylamide beads, latex beads, dimethylacrylamide beads optionally cross-linked with N,N'-bis-acryloyl ethylene diamine, glass particles coated with hydrophobic polymer, etc., i.e., material having a rigid or semi-rigid surface;

b) soluble supports such as low molecular weight non-cross-linked polystyrene; and.

c) derivatized forms thereof such as

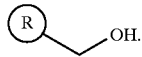

Suitable aminoacid protecting groups are well known in the art and include Fmoc, Alloc (allyloxycarbonyl), etc.

TABLE 1

LINKER GROUPS

| Linker Group | Cleavage Reagent |
|---|---|
| 1. (o-nitrobenzyl –CH₂B– or o-nitrobenzyl –CH₂O–C(O)–B–) | hv |
| 2. (O₂N–aryl–CH₂O–) | hv |
| 3. (aryl with OR and O–) | Ce(NH₄)₂(NO₃)₆ |
| 4. (RO–aryl–O–) | Ce(NH₄)₂(NO₃)₆ |
| 5. —CH=CH(CH₂)₂— | O₃, OsO₄/IO₄⁻, or KMnO₄ |
| 6. —CH=CHCH₂— | O₃, OsO₄/IO₄⁻, or KMnO₄ |
| 7. —CH₂CH=CH— | O₃, OsO₄/IO₄⁻, or KMnO₄ |
| 8. (furan-O–) | 1) O₂ or Br₂, MeOH  2) H₃O⁺ |
| 9. —CH=CHCH₂O— | (Ph₃P)₃RhCl(H) |

TABLE 1-continued

LINKER GROUPS

| Linker Group | Cleavage Reagent |
|---|---|
| 10. 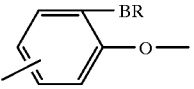 | Li, Mg, or BuLi |
| 11. —S—$CH_2$—O— | $Hg^{+2}$ |
| 12. 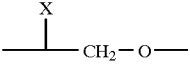 | Zn or Mg |
| 13. 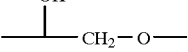 | Oxidation, e.g., $Pb(OAc)_4$ or $H_5IO_6$ |
| 14. 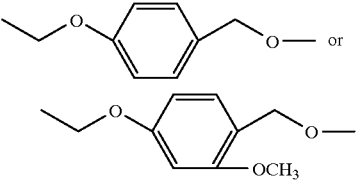 | $H_3O^+$ |

R = H or lower alkyl; B = O or NH: and X = electron withdrawing group such as Br, Cl, and I.

Optical Isomers—Diastereomers—Geometric Isomers

Some of the compounds described herein contain one or more asymmetric centers and may thus give rise to enantiomers, diastereomers, and other stereoisometric forms which may be defined in terms of absolute stereochemistry as (R) or (S), or as (D) or (L) for amino acids. The present invention is meant to include all such possible diastereomers as well as their racemic and optically pure forms. Optically active (R) and (S), or (D and L), isomers may be prepared using chiral synthons or chiral reagents, or resolved using conventional techniques. When the compounds described herein contain olefinic double bonds or other centers of geometric asymmetry, and unless specified otherwise, it is intended to include both E and Z geometric isomers. Likewise, all tautomeric forms are intended to be included.

Utility

The library of the present invention is useful as a screening tool for discovering new lead structures by evaluation across an array of biological assays, including the discovery of selective inhibition patterns across isozymes. The library is thus a tool for drug discovery; i.e., as a means to discover novel lead compounds by screening the library against a variety of biological targets and to develop structure-activity relationships (SAR) in large families of related compounds. The library may be tested with the ligands attached to the solid supports as depicted in Formula I or I', or the compounds II may be detached prior to evaluation. With the compounds of Formula I or I', screening assays such as FACS sorting and cell lawn assays may be used. When a compound is detached prior to evaluation, its relationship to its solid support is maintained, for example, by location within the grid of a standard 96-well plate or by location of activity on a lawn of cells. Whether the compounds are tested attached or detached from the solid supports, the tags attached to solid support associated with bioactivity may then be decoded to reveal the structural or synthetic history of the active compound (Ohlmeyer et al., Proc. Natl. Acad Sci. USA, 90, 10922–10926, December 1993 and Still et al., Complex Combinatorial Chemical Libraries Encoded with Tags, WO 94/08051) or, alternatively, the structures may be determined by deconvolution. The usefulness of such a library as a screening tool is demonstrated by Burbaum et al., Proc. Natl. Acad. Sci. USA, 92, 6027–6031, June 1995, who describe the assaying of encoded combinatorial libraries for, e.g., carbonic anhydrase inhibition. Even if no compounds are found to be active in a given screen, such lack of activity often provides useful SAR information.

Assays for Determining Biological Activity

Assays for evaluating the compounds of the present invention are well known in the art. Although one usually does not know a priori in which specific assays a particular compound or group of library compounds will have activity, a useful system for screening libraries of the format of that described in the present invention, to identify activities with respect to a wide variety of enzymes and molecular targets, is disclosed in U.S. Ser. No. 08/553,056, filed Nov. 3, 1995, now U.S. Pat. No. 5,856,083.

Methods of Synthesis

The compounds of the present invention can be prepared according to the following methods. At each step in the synthesis each solid support upon which a compound is being synthesized may be uniquely tagged to define the particular chemical event(s) occurring during that step. The tanging is accomplished using identifiers such as those of Formula IV, which record the sequential events to which the support is exposed during the synthesis, thus providing a reaction history for the compound produced on each support. The identifiers are used in combination with one another to form a binary or higher order encoding scheme permitting a relatively small number of identifiers to encode a relatively large number of reaction products. For example, when used in a binary code, N identifiers can encode up to $2^N$ different compounds and/or conditions. By associating each variable or combination of variables at each step of the synthesis with a combination of identifiers which uniquely define the chosen variables such as reactant, reagent, reaction conditions, or combinations of these, one can use the identifiers to define the reaction history of each solid support.

In carrying out the syntheses, one begins with at least $10^4$, desirably at least $10^7$, and generally not exceeding $10^{15}$ solid supports. Depending on the pre-determined number of choices for the first step, one divides the supports accordingly into as many containers. The appropriate reagents and reaction conditions are applied to each container and the combination of identifiers which encode for each step 1 choice is added and attached. Depending on the chemistries involved, the tagging may be done prior to, concomitantly with, or after the reactions which comprise each choice. As a control, sample supports may be picked at any stage and a portion of their tags detached and decoded to verify that the correct tags are bound to the sample supports. As needed, one may wash the beads free of any excess reagents or by-products before proceeding. At the end of each step, the supports are combined, mixed, and again divided, this time into as many containers as pre-determined for the number of choices for the second step in the synthesis. This procedure of dividing, reacting, tagging, and remixing is repeated until the combinatorial synthesis is completed.

As an example of the synthesis via ring closure for the preparation of four compounds of Formula I, but excluding the tagging steps, resin-linked α-amino ester of the formula:

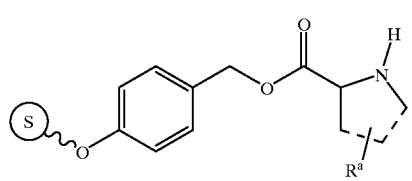

A is suspended in an aprotic, polar solvent such methylene chloride, DMF, THF or ethyl acetate. An excess of a soluble organic base such as triethylamine, N,N-diisopropylethylamine, or pyridine is added to the suspended resin. This mixture is treated with an excess of an appropriately substituted 2-azidobenzoyl chloride of the formula:

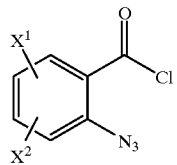

and agitated at room temperature to produce a resin linked N-(2-azidobenzoyl)amino ester of the formula:

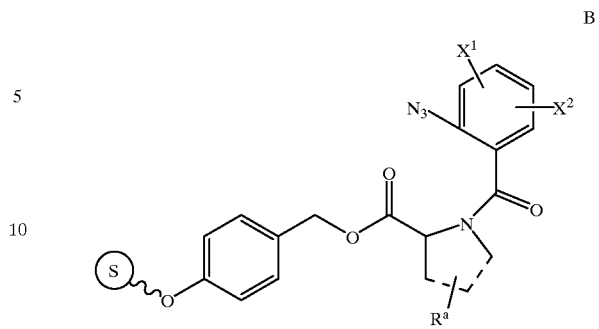

B

The resin is filtered and washed and then suspended in an involatile solvent (i.e., a non-protic, organic solvent with a boiling point of 80–140° C.) such as toluene, xylene, or chlorobenzene and treated with an excess of a trivalent phosphorus reagent such as triphenylphosphine or tributylphosphine. This mixture is agitated and heated to 80–140° C. for 2–24 hr, then cooled to produce a resin-linked 1,4-benzodiazepin-5-one of the formula:

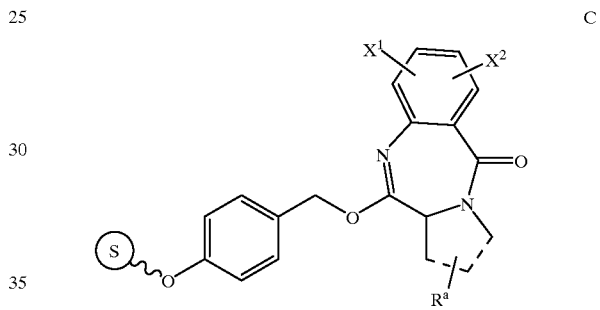

C which is washed and then is suspended in an acidic solution and agitated at room temperature for 1–24 hr. The resin is filtered and washed and the filtrate and washings are combined and evaporated to give a 1,4-benzodiazepin-2,5-dione of the formula:

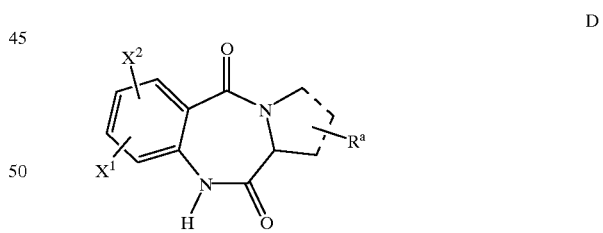

D wherein $X^1$, $R^2$, and $R^a$ are selected such that formula D represents compounds of the formulae:

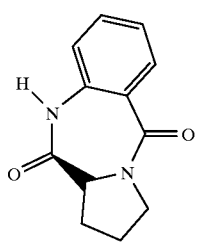

4

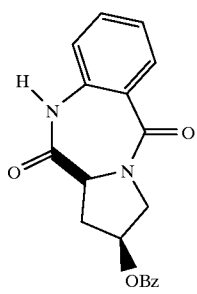

8

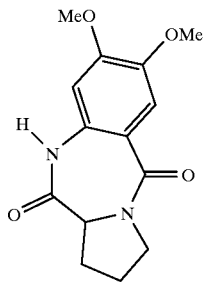

11

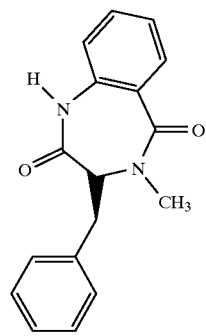

16

Compounds 4, 8, 11, and 16 have been synthesized by the aza-Wittig method of the present invention. Compound 4 is a known intermediate useful in the synthesis of antitumor antibiotics (Kaneko et al., Tet. Lett., 1983, p. 5165; Kaneko et al., J. Med. Chem., 1985, p. 388). Compound 8 is a novel compound useful as an intermediate in the synthesis of the antibiotic 5-thioabbeymycin (Kamal et al, Bioorg. Med. Chem. Lett., 3, p. 743, 1993) and abbeymycin. Compound 11 is a novel compound useful as an intermediate in the synthesis of antitumor antibiotics (Hurley et al., Chem. Res. Toxicol, 1, p. 258, 1988. Compound 16 is a natural product isolated from *Penicillium cyclopium* with potential antibiotic properties (Framm et al., Eur. J. Biochem, 37, p. 78, 1973.)

Scheme 1

Resin-linked α-amino ester, A, is suspended in an aprotic, polar solvent such methylene chloride, DMF, THF or ethyl acetate. An excess (2–50 equivalents) of a soluble organic base such as triethylamine, N,N-diisopropylethylamine, or pyridine is added to the suspended resin. Optionally, an acylation catalyst such as 4-dimethylaminopyridine may be added. This mixture is treated with an excess (2–10 equivalents) of an appropriately substituted 2-azidobenzoyl chloride and agitated at room temperature for 2–24 hr. The resin is filtered and washed multiple times with an appropriate solvent such as methylene chloride to remove excess reagents and byproducts. Resin linked N-(2-azidobenzoyl) amino ester, B, is suspended in an involatile solvent such as toluene, xylene, or chlorobenzene and treated with an excess (2–10 equivalents) of a trivalent phosphorus reagent such as triphenylphosphine or tributylphosphine. This mixture is agitated and heated to 80–140° C. for 2–24 hr, then cooled and the resin-linked 1,4-benzodiazepin-5-one, C, is washed multiple times with appropriate solvents such as methylene chloride or toluene to remove excess reagents and byproducts. Resin-linked 1,4-benzodiazepin-5-one, C, is suspended in an acidic solution such as trifluoroacetic acid/methylene chloride (50–90% $TFA/CH_2Cl_2$) or hydrogen chloride/dioxane (1–4M HCl/dioxane) and agitated at room temperature for 1–24 hr. The resin is filtered and washed with appropriate solvents such as methylene chloride or dioxane. The filtrate and washings are combined and evaporated to give the crude 1,4-benzodiazepin-2,5-dione, D, which may be purified and characterized by standard techniques.

SCHEME 1

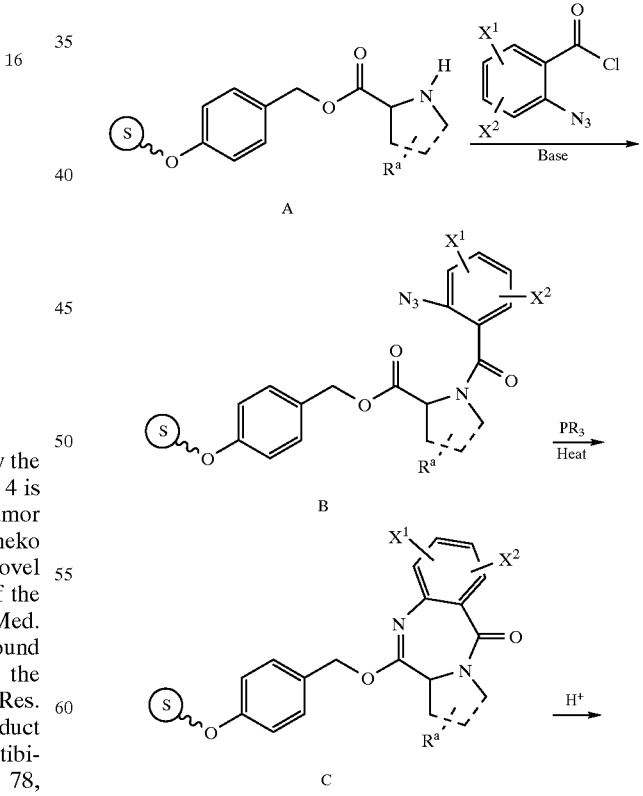

-continued

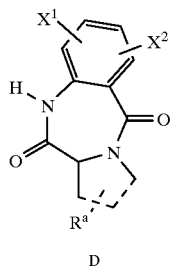

D

The invention is further defined by reference to the following examples, which are intended to be illustrative and not limiting.

PREPARATION 1

IDENTIFIERS

Twelve compounds of the general formula:

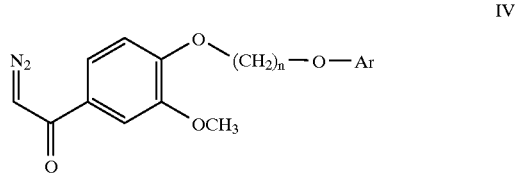

IV wherein:

n=3–12 and Ar is pentachlorophenyl or n=54–6 and Ar is 2,4,6-trichlorophenyl were prepared according to Scheme 6 and the following illustrative example.

a) Methyl vanillate (0.729 g, 4.0 mmole), 1-hydroxy-9-(2,3,4,5,6-pentachlorophenoxy)nonane (1.634 g, 4.0 mmole) and triphenylphosphine (1,258 g, 4.8 mmole) were dissolved in 20 mL dry toluene under argon. DEAD (0.76 mL, 0.836 g, 4.8 mmole) was added dropwise and the mixture was stirred at 25° C. for one hr. The solution was concentrated to half volume and purified by flash chromatography eluting with DMC to give 1.0 g (1.7 mmole, 43%) of the product as a white crystalline solid.

b) The methyl ester from Step (a) (1.0 g, 1.7 mmole) was dissolved in 50 mL THF, 2 mL water was added, followed by LiOH (1.2 g, 50 mmole). The mixture was stirred at 25° C. for one hr. then refluxed for 5 hr. After cooling to 25° C., the mixture was poured onto ethyl acetate (200 mL) and the solution was washed with 1 M HCl (3×50 mL) then sat'd aq. NaCl (1×50 mL) and dried over sodium sulfate. The solvent was removed and the crude acid azeotroped once with toluene.

c) The crude material from Step (b) was dissolved in 100 mL toluene, 10 mL (1.63 g, 14 mmole ) thionyl chloride was added, and the mixture was refluxed for 90 min. The volume of the solution was reduced to approx. 30 mL by distillation, then the remaining toluene was removed by evaporation. The crude acid chloride was dissolved in 20 mL dry DCM and cooled to −70° C. under argon and a solution of approx. 10 mmole diazomethane in 50 mL anhydrous ether was added. The mixture was warmed to r.t. and stirred for 90 min. Argon was bubbled through the solution for 10 min., then the solvents were removed by evaporation and the crude material was purified by flash chromatography, eluting with 10–20% ethyl acetate in hexane. The diazoketone (0.85 g, 1.4 mmole, 82% yield over three steps) was obtained as a pale yellow solid.

An improvement was made to the final diazomethylation step, whereby the acid chloride was reacted with (trimethylsilyl)-diazomethane and triethylamine to give the identifier, which was then used without further purification. This was a significant improvement over the original reaction with diazomethane, as the identifier was now obtained in high yield with no chlorometylketone byproduct. Also, purification by flash chromatography was no longer necessary, which in some cases had resulted in significant acid-catalyzed decomposition of the identifier.

Alternate Step c) To a solution of the acyl chloride (3.8 mmol, 1.00 eq.) and 1.85 mL (13.3 mmol, 3.50 eq.) of triethylamine in anhydrous THF/acetonitrile (1:1) at 0° C. under argon was added 5.7 mL (11.4 mmol, 3.00 eq.) of a 2.0 M solution of (trimethylsilyl)-diazomethane in hexanes. The resulting orange solution was stirred at 0° C. for 2 hr, then at 25° C. for 17 hr. (If a precipitate formed immediately upon addition of (trimethylsilyl)diazomethane, $CH_2Cl_2$ was added until the precipitate redissolved). EtOAc was added (250 mL), and the organic layer washed with saturated aq. $NaHCO_3$ (100 mL) and $H_2O$ (100 mL), then dried (anhydrous $MgSO_4$). Removal of the volatiles in vacuo gave the product as yellow crystals in 60–100% yield.

The other 11 identifiers of Formula IV were prepared by analogous synthetic routes, steps (a), (b), and (c).

In the synthesis of Example 5, the 12 identifiers were used to encode the combinatorial library. In Step 1, pentachlorophenyl identifiers where n=7–12 (abbreviated $C_7Cl_5$, $C_8Cl_5$ , . . . , $C_{12}Cl_5$) were used in the following binary encoding scheme: 000001=(n=12), 000100=(n=11) though 100000=(n=7). In Step 2, pentachlorophenyl identifiers where n=6–9 (abbreviated $C_6Cl_5$, $C_7Cl_5$, $C_8Cl_5$, and $C_9Cl_5$) were used and encoded as follows: 000001=(n=6), 000010= (n=5), 000100=(n=4), and 00100=(n=3). Also in Step 2, trichlorophenyl identifiers where n=4–6 (abbreviated $C_4Cl_3$, $C_5Cl_3$, and $C_6Cl_3$) were used and encoded as follows: 01000=(n=6). Step 3 was not encoded.

Thus, in Step 1 reagent 3 is encoded "011" which represents tagging this choice in the synthesis with the two pentachlorophenyl identifiers where n=11 and 12. Likewise, in Step 3 reagent 30 is encoded "01110" which represents tagging this choice in the synthesis with the pentachlorophenyl identifiers where n=3–6 and the trichlorophenyl identifier where n=6.

SCHEME 6
IDENTIFIERS

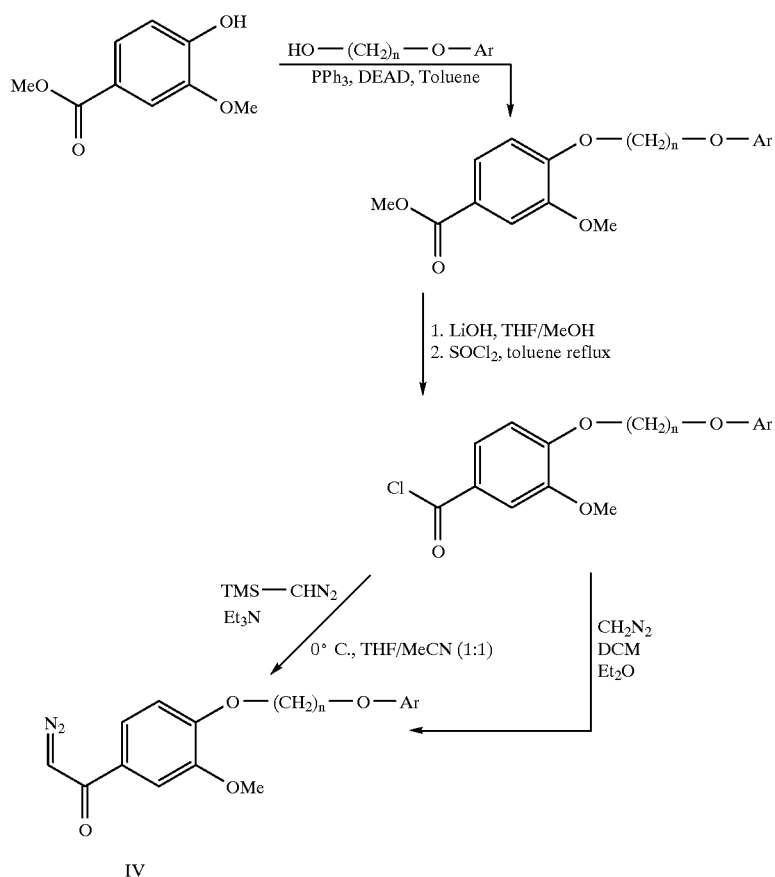

PREPARATION 1

N-Fmoc-cis4-benzoyloxy-L-proline-p-alkoxybenzyl Resin

N-Fmoc-cis-4-benzoyloxy-L-proline p-alkoxybenzyl resin, 5, was prepared by routine methods as outlined below.

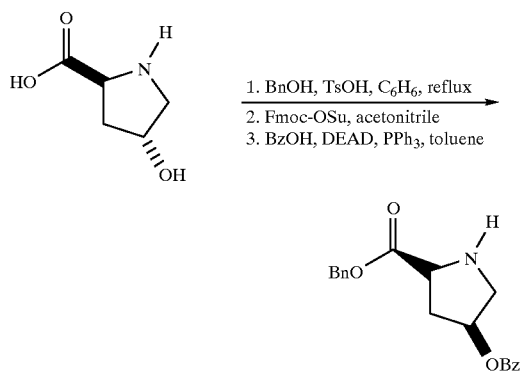

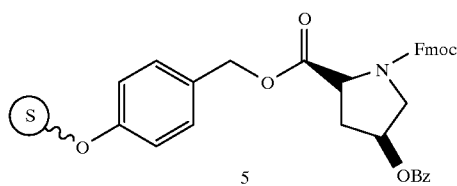

PREPARATION 2

BIS-LINKER ATTACHMENT

TENTAGEL resin may be modified with bis-Fmoc lysine to increase the available reaction sites for ligand attachment. For purposes of simplicity, the schemes elsewhere herein do not show the use of this modification with lysine.

1) Preparation of 4-acetoxymethylphenoxy acetic acid: A solution of 4-hydroxymethyl-phenoxy acetic acid (9.9 g, 55 mmol) in pyridine (200 mL) was treated with acetic anhydride (22.15 g, 218 mmol, 4 equiv.), and the reaction mixture was stirred 25° C. under argon for 48 hr. The reaction mixture was concentrated in vacuo to ~25 mL, then diluted with 200 mL of EtOAc, and placed in a separatory funnel. The resulting suspension was treated with ca. 50 mL of 1N aq. HCl, and shaken. The pH of the aqueous layer was checked, and adjusted to pH 2 with portionwise addition of conc. HCl and shaking. The layers were separated. The organic layer was washed with brine, then dried (MgSO$_4$), and concentrated in vacuo to afford crude product as a reddish-brown oil. This material was purified by flash chromatography, eluting with ethyl acetate/hexanes (1:9), followed by ethyl acetate/hexanes (1:1) to afford 7.0 g (57%) of 4acetoxymethyl-phenoxy acetic acid as an off-white solid.

TLC: Rf=0.2, silica gel, 100% EtOAc (UV). $^1$H-NMR: (CD$_3$OD) 2.0 (s, 3H), 4.6 (s, 2H), 5.0 (s, 2H), 6.80 (d, 2H), 7.20 (d, 2H).

2) Preparation of resin support A: A 300 mL synthesis vessel was charged with TENTAGEL-S-NH$_2$ resin (25 g, 0.30 mmol/g capacity, (7.5 mmol)), and the beads were washed with 2×150 mL methylene chloride. A solution of N-α-N-ε-diFmoc-lysine (13.3 g, 22.5 mmol, 3 equiv.) in 100 mL of DMF/methylene chloride (1:1), was added to the vessel. The resulting mixture was treated with 4-dimethylamino-pyridine (92 mg, 0.75 mmol, 0.1 equiv.), followed by N,N'-diisopropylcarbodiimide (4.73 g, 37.5 mmol, 5 equiv.), and the reaction mixture was shaken at ambient temperature. After 6 hours, the solvent was removed by filtration, and the beads were washed successively with 5×150 mL DMF, and 5×150 mL methylene chloride. A small portion of the resin was checked by the Kaiser test for disappearance of free NH$_2$, and found to be negative.

The resin was treated with a 30% solution of piperidine in DMF (100 mL), and shaken at 25° C. for 1 hr. The resin was filtered and washed successively with 5×150 mL DMF and 5×150 mL methylene chloride. A small portion of the resin was checked with the Kaiser test to assure removal of the Fmoc groups, and found to be positive.

A suspension of 4-acetoxymethylphenoxy acetic acid (20.2 g, 90 mmol, 6 equiv.) in 60 mL of methylene chloride was treated with DMF dropwise until all solid went into solution. This solution was then added to resin above (nom. 15 mmol) in a 300 mL synthesis vessel. The resulting suspension was treated with 4-dimethylaminopyridine (366 mg, 3.0 mmol, 0.2 equiv.), followed by N,N'-diisopropylcarbodiimide (18.9 g, 150 mmol, 10 equiv.), and the reaction mixture was shaken at 25° C. for 16 hr. The solvent was removed by filtration, and the resin was washed successively with 5×150 mL DMF and 5×150 mL CH$_2$Cl$_2$ to afford the acetate protected resin. A small aliquot of the resin was checked for disappearance of free NH$_2$ with the Kaiser test, and found to be negative.

The acetate protected resin from above was treated with a solution of 10% hydrazine hydrate in methanol (100 mL), and shaken at ambient temperature. After 6 hr., the solvent was removed by filtration, and the resin was washed successively with 5×150 mL MeOH and then re-treated with 10% hydrazine hydrate in MeOH (100 mL) and shaken at 25° C. for 16 hr. The solvent was removed by filtration, and the resin was washed successively with 5×150 mL DMF and 5×150 mL CH$_2$Cl$_2$ to afford the hydroxy resin A.

Bis-Linker Attachment

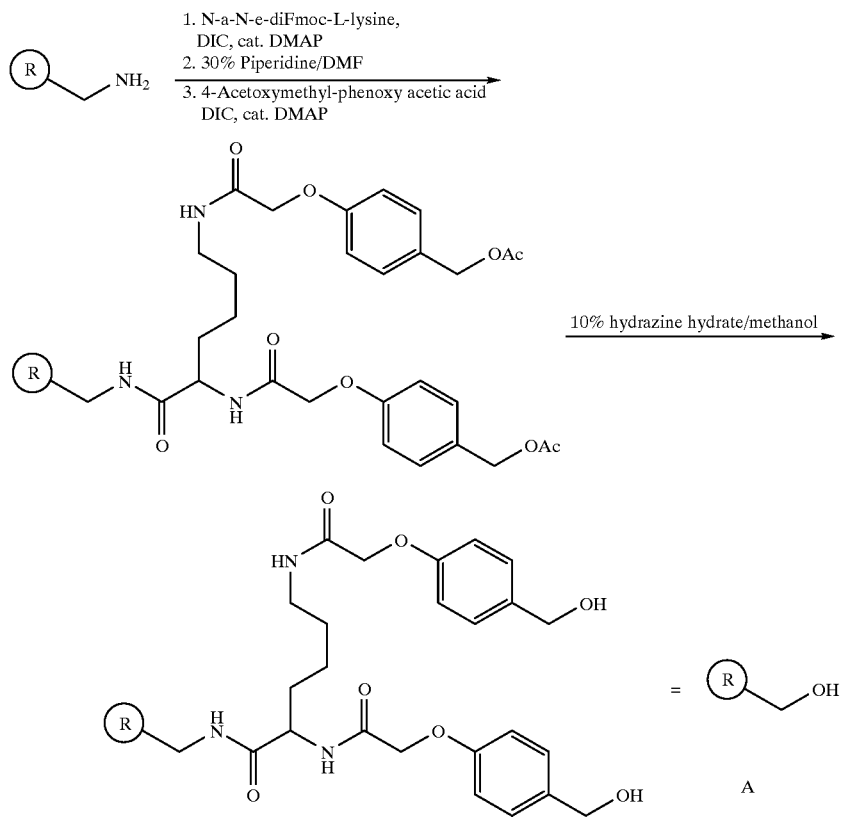

EXAMPLE 1

(11aS)-1,2,3,10,11,11a-Hexahydro-5H-pyrrolo[2,1-c](1,4)-benzodiazepine-5,1-dione

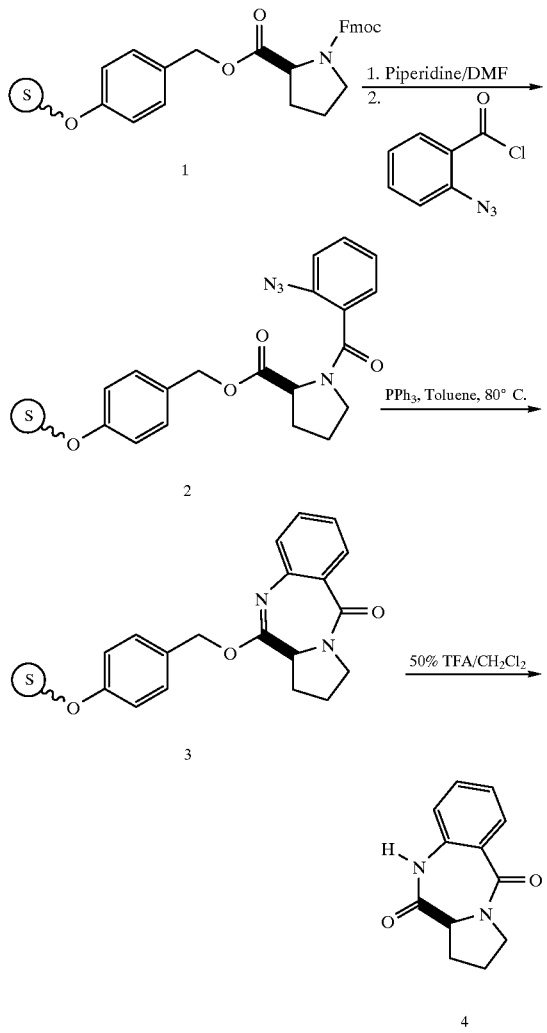

N-Fmoc-L-proline p-alkoxybenzyl resin, 1, (Bachem) (0.34 mmole/g, 2.0 g, 0.68 mmole) was suspended in 30 mL DMF, then filtered. The resin was then shaken with 50% piperidine/DMF for 2 hr. then filtered and washed with DMF (5×30 mL) and methylene chloride (10×30 mL). The resin was suspended in 20 mL methylene chloride, and 2 mL (14 mmole) triethylamine was added, followed by 1.0 g (5.5 mmole, 8 equiv.) 2-azidobenzoyl chloride. The mixture was shaken at 25° C. for 3 hr. and then the resin was washed with methylene chloride (10×30 mL) followed by toluene (10×30 mL). The resin, 2, was suspended in 20 mL toluene and 0.3 g (1.14 mmole, 1.7 equiv.) triphenylphosphine was added and the mixture was shaken until the triphenylphosphine had dissolved. The mixture was shaken and heated to 80° C. for 3 hr. then cooled and washed with methylene chloride (10×30 mL). The pale brown resin, 3, was dried under vacuum.

The resin, 3 (2.0 g, 0.68 mmole), prepared as described above, was suspended in 20 mL methylene chloride and 20 mL trifluoroacetic acid was added. The resin was shaken at 25° C. for 30 min then filtered and washed with methylene chloride (2×20 mL). The filtrate and washings were collected and combined, then evaporated to give the crude product. The benzodiazepine was purified by flash chromatography, eluting with 60% ethyl acetate/hexane to give the product, 4, as a white solid.

$^1$H NMR (300 MHz, CDCl$_3$): δ 2.03 (m, 3H), 2.77 (m, 1H), 3.62 (m, 1H), 3.80 (m, 1H), 4.08 (m, 1H), 7.07 (m, 1H), 7.26 (m, 1H), 7.48 (m, 1H), 8.00 (d, 1H, J=7.7 Hz), 9.07 (br s, 1H, N<u>H</u>); $^{13}$C NMR (125 MHz, CDCl$_3$): δ 23.45, 26.12, 47.26, 56.66, 121.81, 124.90, 127.03, 131.02, 132.34, 135.44, 165.41, 171.40; CIMS: 217 (MH$^+$)

EXAMPLE 2

(2S, 11aS)-2-Benzoyloxy-1,2,3,10,11,11a-hexahydro-5H-pyrrolo-[2,1-c](1,4)-benzo-diazepine-5,11-dione

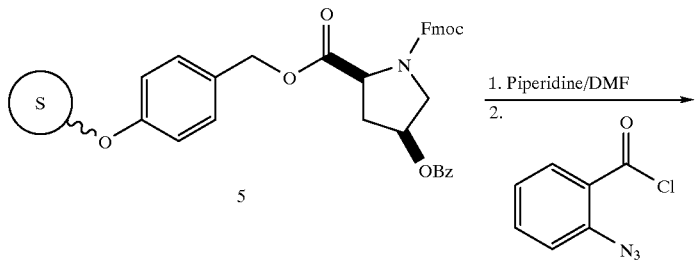

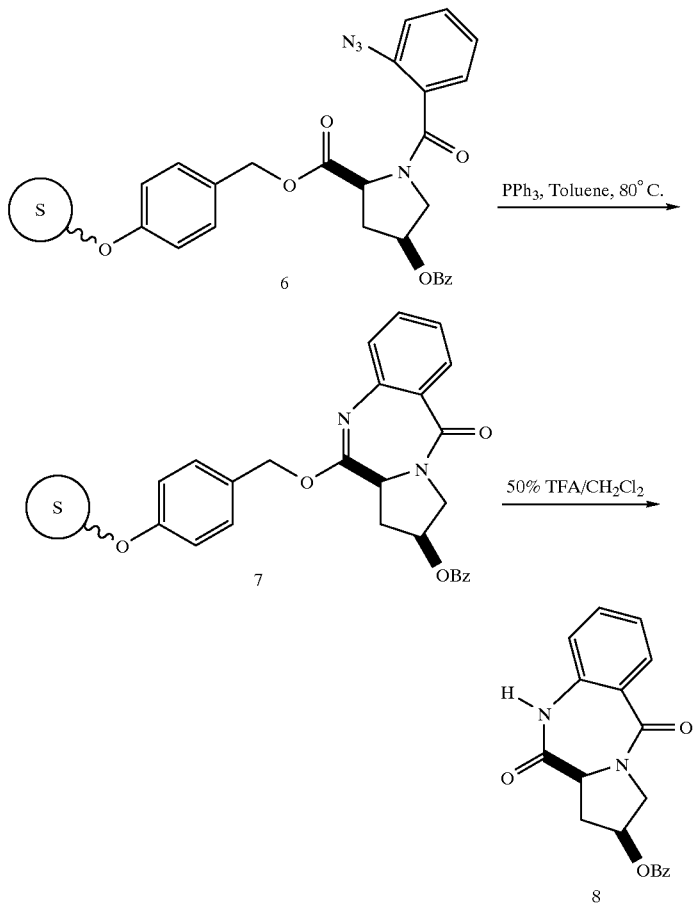

N-Fmoc-cis-4-benzoyloxy-L-proline p-alkoxybenzyl resin, 5, (400 mg) was suspended in 10 mL DMF, then filtered. The resin was then shaken with 50% piperidine/DMF, 10 mL, for 2 hr. then filtered and washed with DMF (5×10 mL) and methylene chloride (10×10 mL). The resin was suspended in 10 mL methylene chloride, 0.4 mL (~3 mmole) triethylamine was added, followed by 0.2 g (1.1 mmole) 2-azido-benzoyl chloride. The mixture was shaken at 25° C. for 12 hr. and then the resin was washed with methylene chloride (10×10 mL), followed by toluene (10× 10 mL). The resin, 6, was suspended in 50 mL toluene and 0.20 g (0.8 mmole) triphenylphosphine was added and the mixture was shaken until the triphenylphosphine had dissolved. The mixture was shaken and heated to 80° C. for 2 hr. then cooled and washed with toluene (5×10 mL) and methylene chloride (10×10 mL). The resin, 7, was dried under vacuum.

The resin, 7, prepared as described above, was suspended in 5 mL methylene chloride and 5 mL trifluoroacetic acid was added. The resin was shaken at 25° C. for 30 min then filtered and washed with methylene chloride (2×10 mL). The filtrate and washings were collected and combined, then evaporated to give the crude product which was purified by flash chromatography eluting with 50% ethyl acetate/hexane to give the product, 8, as a white solid $^1$H NMR (300 MHz, CDCl$_3$): δ 2.41 (m, 1H), 3.31 (d, 1H, J=14.4 Hz), 3.94 (m, 1H), 4.16 (m, 2H), 5.58 (m, 1H), 6.84 (d, 1H, J=8.1 Hz), 7.07 (m, 2H), 7.20–7.37 (m, 3H), 6.47 (s, 1H), 7.87 (d, 1H, J=8.1 Hz), 8.10 (d, 1H, J=7.71 Hz), 9.94 (br s, 1H, N<u>H</u>); $^{13}$C NMR (125 MHz, CDCl$_3$): δ 31.64, 53.18, 56.06, 71.93, 120.88, 124.67, 125.75, 127.87, 129.33, 129.50, 131.06, 132.73, 133.25, 135.61, 165.86, 165.95, 171.93; CIMS: 337 (MH$^+$)

EXAMPLE 3

(11aS)-7,8-Dimethoxy-1,2,3,10,11,11a-hexahydro-5H-pyrrolo[2,1-c]-(1,4)-benzo-diazepine-5,11-dione

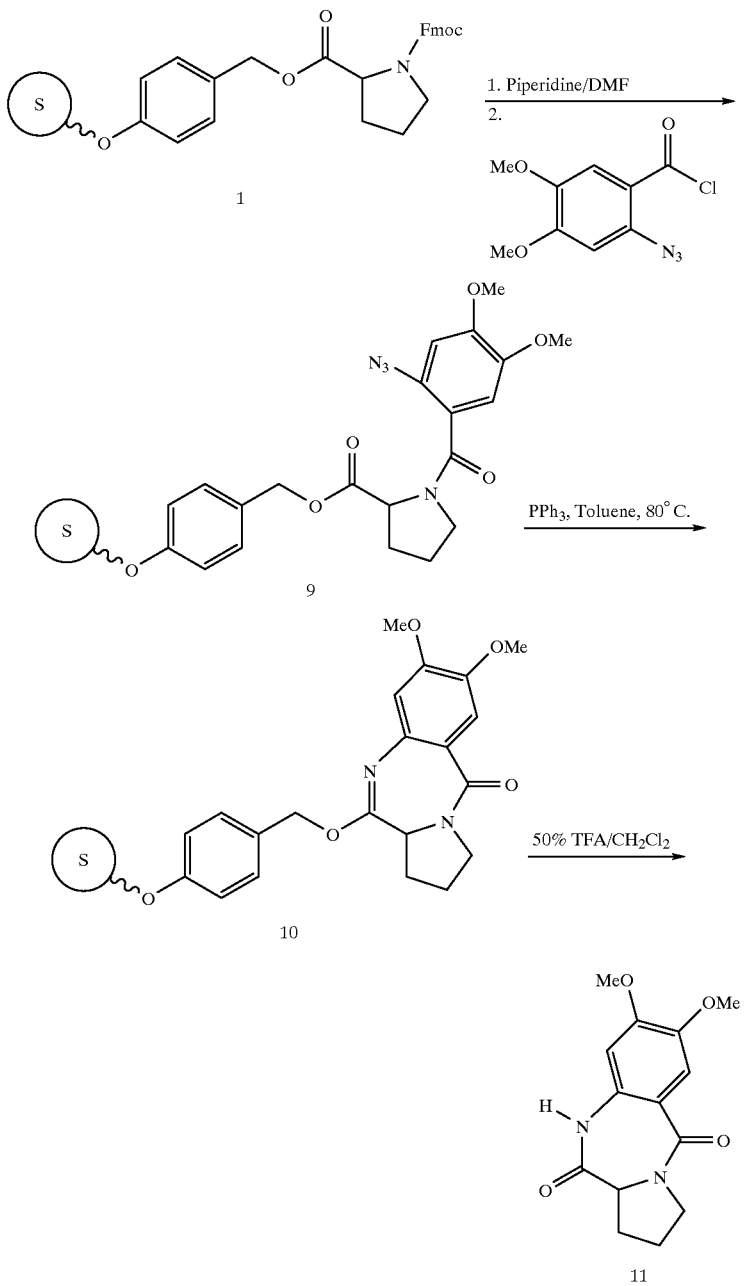

N-Fmoc-L-proline p-alkoxybenzyl resin, 1, (0.34 mmole/g, 5.0 g, 1.8 mmole) was suspended in 50 mL DMF, then filtered. The resin was then shaken with 50% piperidine/DMF for 2 hr. then filtered and washed with DMF (5×50 mL) and methylene chloride (10×50 mL). The resin was suspended in 50 mL methylene chloride, 3 mL (21 mmole) triethylamine was added, followed by 0.75 g (3 mmole, 1.7 equiv.) 2-azido-4,5-dimethoxybenzoyl chloride as a solid. The mixture was shaken at 25° C. for 12 hr. and then the resin was washed with methylene chloride (10×50 mL), followed by toluene (10×50 mL). The resin, 9, was suspended in 50 mL toluene and 1.26 g (4.8 mmole 2.6 equiv.) triphenylphosphine was added and the mixture was shaken until the triphenylphosphine had dissolved. The mixture was shaken and heated to 80° C. for 2 hr. then cooled and washed with toluene (10×50 mL), alternately with methanol and methylene chloride (5×50 mL each) and finally methylene chloride (5×50 mL). The pale brown resin, 10, was dried under vacuum.

A 1.0 g (~0.34 mmole) portion of the resin, 10, prepared as described above, was suspended in 20 mL methylene chloride and 20 mL trifluoroacetic acid was added. The resin was shaken at 25° C. for 30 min then filtered and washed with methylene chlorid e (2×20 mL). The filtrate and washings were collected and combined, then evaporated to give the crude product. The benzodiazepine was purified by flash chromatography eluting with ethyl acetate to give the product, 11, as an off white solid.

$^1$H NMR (300 MHz, CDCl$_3$): δ 2.03 (m, 3H), 2.75 (m, 1H), 3.61 (m, 1H), 3.78 (m, 1H), 3.91 (s, 3H), 3.93 (s, 3H), 4.04 (d, 1H, J=6 Hz), 6.47 (s, 1H), 7.46 (s, 1H), 8.30 (br s,

1H, NH); $^{13}$C NMR (125 MHz, CDCl$_3$): δ 23.49, 26.11, 47.26, 56.05, 56.11, 56.80, 103.85, 112.01, 119.16, 129.79, 146.27, 152.20, 165.27, 171.13; CIMS: 277 (MH$^+$)
EXAMPLE 4
Cyclopeptin
p-Alkoxybenzyl alcohol resin, 12, 2.5 g (1.0 mmole/g) was suspended in 30 mL methylene chloride. N-Fmoc-N-methyl-L-phenylalanine, 3.0 g (7.5 mmole, 3 equiv.), DMAP, 1.0 g (0.82 mmole, 0.3 equiv.), and DIC 1.74 mL (1.26 g, 10 mmole, 4 equiv.) were added and the mixture was agitated for 2 hr. The resin was filtered and washed with methylene chloride, (10×30 mL), then dried.
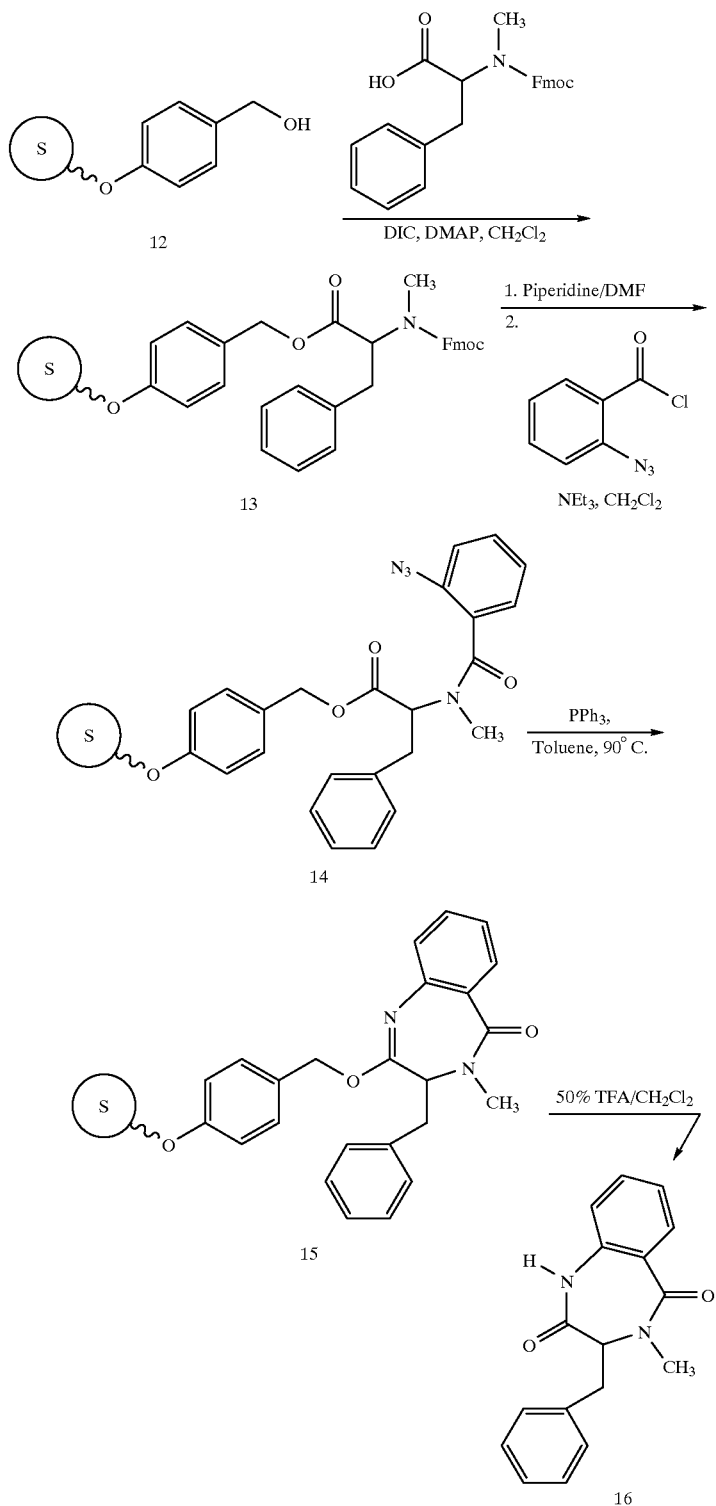

The N-Fmoc-N-methyl-L-phenylalanine p-alkoxybenzyl ester resin, 13, 1.0 g was suspended in 50% piperidine/DMF, 30 mL, and agitated for 2 hr, then filtered and washed with DMF (5×30 mL) and methylene chloride (10×30 mL). The resin was suspended in 20 mL methylene chloride; 1.0 mL (~07 mmole) triethylamine was added followed by 0.6 g (3.3 mmole) 2-azido-benzoyl chloride. The mixture was shaken at 25° C. for 1 hr and then the resin was washed with methylene chloride (10×30 mL) followed by toluene (10×30 mL). The resin, 14, was suspended in 20 mL toluene and 0.52 g (2.0 mmole) triphenylphosphine was added and the mixture was shaken until the triphenylphosphine had dissolved. The mixture was shaken and heated to 90° C. for 3 hr then cooled and washed with toluene (5×20 mL) and methylene chloride (10×20 mL) to give the resin linked 1,4-benzodiazepine-5-one, 15.

The resin, 15, was suspended in 10 mL methylene chloride and 10 mL trifluoroacetic acid was added. The resin was shaken at 25° C. for 2 hr, then filtered and washed with methylene chloride (2×20 mL). The filtrate and washings were collected and combined, then evaporated to give the crude product which was purified by flash chromatography eluting with 50% ethyl acetate/hexane to give the product, 16.

$^1$H NMR (300 MHz, DMSO-d$_6$, 100° C.): δ 2.91–3.06 (m, 2H), 2.95 (s, 3H), 4.30 (t, 1H, J=7.9 Hz), 7.13–7.28 (m, 7H), 7.48 (m, 1H), 7.80 (d, 1H, J=7.7 Hz), 10.22 (br s, 1H, N$\underline{H}$); CIMS: 281 (MH$^+$)

EXAMPLE 5

Synthesis of 1,4-Benzodiazepin-2,5-dione Library

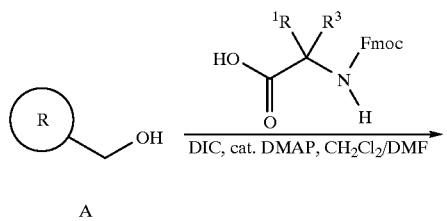

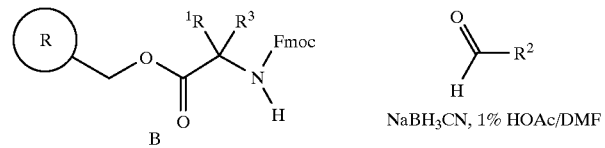

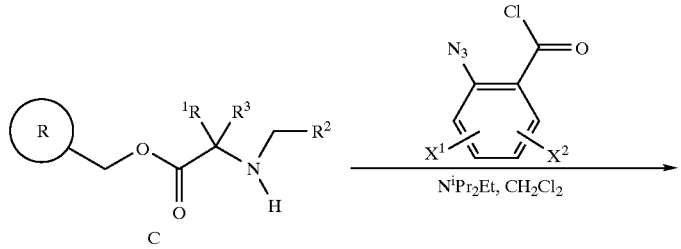

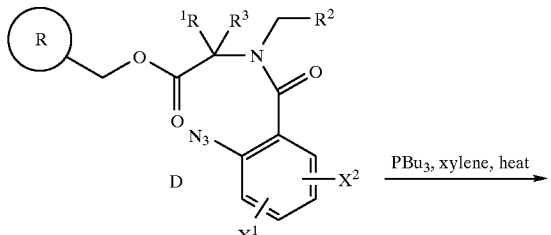

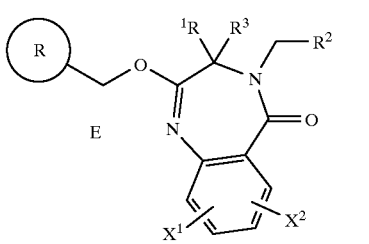

-continued
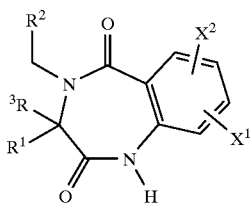
F
α-Amino acids (Reagent Set 1),
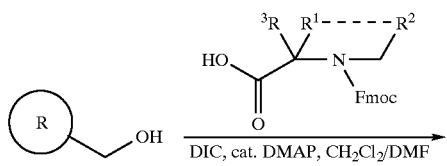
A
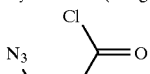
2-Azidobenzoyl chloride (Reagent Set 3)
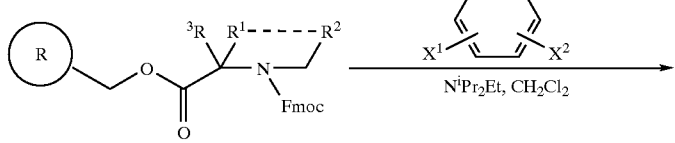
B
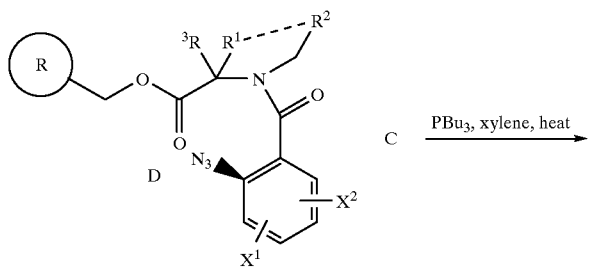
C
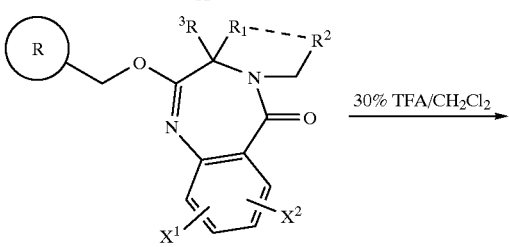
D
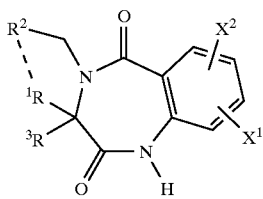
E
A 1.2 g (0.53 mmole/g, 0.64 mmole OH) portion of p-alkoxybenzyl resin A, was placed in each of 46 separate 100 mL synthesis vessels (vessels 1–46). The resin in each vessel was suspended in 30 mL methylene chloride, agitated for 5 min and then filtered. The solvated resin was resuspended in 20 mL methylene chloride. Solutions of 46 protected α-amino acids (Reagent Set 1, 4.3 mmole, ~7 equiv), prepared in 20 mL 1:1 methylene chloride:DMF, were added to the vessels, one solution per vessel, containing the suspended resin. The vessels were agitated for 5 min, then 2 mL of 45 mg/mL DMAP (90 mg, 0.73 mmole, 1.2 equiv) solution in methylene chloride was added to each vessel and the mixtures were agitated for 5 min. DIC, 1.1 mL (91 mg, 7.2 mmole, 11 equiv), was added to each vessel and the mixtures were agitated for 14 hr. Then the resin batches, B, were filtered and washed with 5×40 mL methylene chloride.

The 46 resin batches were encoded with six tags as follows.

(i) The resin batches were suspended in 30 mL methylene chloride. Aliquots, 2 mL of 45 mg/mL (90 mg tag precursor/vessel ~7.5% by mass of resin), $C_{12}C_{15}$ tag precursor solution in methylene chloride were added to the appropriate vessels and the vessels were shaken for 2 min. Aliquots, 2 mL of 45 mg/mL (90 mg tag precursor/vessel ~7.5% by mass of resin), of $C_{11}C_{15}$ tag precursor solution in methylene chloride were added to the appropriate vessels and the vessels were shaken for 2 hr. Rhodium (II) trifluoroacetate dimer, 2 mL of 1 mg/mL in methylene chloride, was added to each vessel in turn with ~30 sec agitation of the vessels after each addition. The resin batches, tag precursor and catalyst were agitated for 12 hr, then filtered and washed with 5×40 mL methylene chloride.

(ii) The procedure from (i) was repeated for tags $C_{10}Cl_5$ and $C_9Cl_5$.

(iii) The procedure from (i) was repeated for $C_8Cl_5$ and $C_7Cl_5$.

The resin batches, encoded 000001–101110, were combined in a seperatory funnel and washed with 5×300 mL methylene chloride. The resin was then filtered and dried for 12 hr in vacuo.

The resin above was divided into two equal batches of 1.75 g which were placed into two separate 100 mL synthesis vessels (vessels 1 and 2) and sixty equal batches of 0.85 g which were placed into sixty separate 100 mL synthesis vessels (vessels 3–62).

The 62 resin batches were encoded with six tags as follows. (iv) The resin batches were suspended in 30 mnL methylene chloride. Aliquots, 2 mL of 37 mg/mL (74 mg tag precursor/vessel ~8.7% by mass of resin), of $C_6Cl_5$ tag precursor solution in methylene chloride were added to the appropriate vessels from 3 to 62 and the vessels were shaken for 2 min. A 3 mL aliquot of 37 mg/mL $C_6Cl_5$ tag precursor solution was added to vessel 1 (111 mg tag precursor in vessel 1, 6.3% by mass of resin). Aliquots, 2 mL of 37 mg/mL (74 mg tag precursor/vessel ~8.7% by mass of resin), of $C_5Cl_5$ tag precursor solution in methylene chloride were added to the appropriate vessels from 3 to 62 and the vessels were shaken for 2 min. A 3 mL aliquot of 37 mg/mL $C_5Cl_5$ tag precursor solution was added to vessel 2 (111 mg tag precursor in vessel 2, 6.3% by mass of resin). Rhodium (II) trifluoroacetate dimer, 2 mL of 1 mg/mL in methylene chloride, was added to each vessel in turn with ~30 sec agitation of the vessels after each addition. The resin batches, tag precursor and catalyst were agitated for 12 hr, then filtered and washed with 5×40 mL methylene chloride.

(v) The procedure from (iv) was repeated for tags $C_4Cl_5$ and $C_3Cl_5$.

(vi) The procedure from (iv) was repeated for $C_6Cl_3$ and $C_5Cl_3$ with the modification that 4 mL aliquots 37 mg/mL $C_6Cl_3$ and $C_5Cl_3$ tag precursor solutions were used and also a 4 mL aliquot of 37 mg/mL $C_4Cl_3$ tag precursor solution was added to vessel 32.

The resin batches, encoded 000001–111110, were suspended in 30 mL DMF, agitated for 5 min and then filtered. A solution of 30% piperidine in DMF was added to each vessel, the mixtures were agitated for 30 min and then filtered. The resin batches were washed with 2×30 mL DMF, then 2×30 mL 1% acetic acid in DMF and then filtered. The resin batches were resuspended in 20 mL 1% acetic acid in DMF, and 2.4 mmole (~5 equiv) of the appropriate aldehydes (Reagent Set 2), was added, as a solution in 10 mL 1% HOAc/DMF, to each of the vessels 3–62. The mixtures were agitated for 2 hr then 5 mL of 1M sodium cyanoborohydride (5 mmole, 10 equiv) in THF was added to each of the vessels. The quantity of aldehyde, and volume of sodium cyanoborohydride solution was doubled for vessels 1 and 2. The mixtures were shaken for a further 90 min, then filtered and washed with 2×30 mL DMF and 5×30 mL methylene chloride to give resin batches C.

A collection of 51 319 1,4benzodiazepine-2,5-diones was prepared as follows. Resin batches 3C–62C were combined and mixed thoroughly in a seperatory funnel, then divided as a slurry in methylene chloride into nineteen equal portions (~2.7 g, 1.4 mmole) in 100 mL synthesis vessels. The resin was suspended in 30 mL methylene chloride and diisopropylethylamine, 2.5 mL (1.8 g, 14 mmole, 10 equiv), was added followed by 5 mmole of the appropriate o-azidobenzoyl chloride (Reagent Set 3). The mixtures were shaken at room temperature for 16 hr and then filtered and washed with 5×30 mL methylene chloride and 2×30 mL xylene to give resin batches D. Each resin batch was transferred as a slurry into separate 50 mL flasks and the suspensions were sparged with argon for 5 min, then sealed with a septum. Tributylphosphine, 1.8 mL (1.45 g, 7.2 mmole, 5 equiv), was added to each flask and the mixtures were heated to 140–150° C. for 6 hr, then cooled, filtered, and washed with 2×30 mL toluene and 5×30 mL methylene chloride to give the resin linked benzodiazepines, E.

The product 1,4-benzodiazepine-2,5-diones, F, were cleaved from the resin support by suspending the resin, 20 beads, in 100 μL of 70% TFA/water for 4 hours and filtering the solution.

A second collection of 1 170 1,4-benzodiazepine-2,5-diones was prepared as follows. Resin batches 1C and 2C were combined and mixed thoroughly in a seperatory funnel. The resin was dried in vacuo and divided into thirteen equal portions (~0.27 g, 0.14 mmole) then placed in 20 mL synthesis vessels. The resin was suspended in 10 mL methylene chloride and diisopropylethylamine, 0.25 mL (0.18 g, 1.4 mmole, 10 equiv), was added followed by 0.5 mmole of thirteen o-azidobenzoyl chlorides. The mixtures were shaken at room temperature for 16 hr and then filtered and washed with 5×10 mL methylene chloride and 2×10 mL xylene to give resin batches D. Each resin batch was transferred as a slurry into separate 25 mL flasks and the suspensions were sparged with argon for 5 min, then sealed with a septum. Tributylphosphine, 0.14 mL (0.11 g, 0.55 mmole, 4 equiv), was added to each flask and the mixtures were heated to 140–150° C. for 6 hr, then cooled, filtered, and washed with 2×10 mL toluene and 5×10 mL methylene chloride to give the resin batches E, from which the product 1,4-benzodiazepine-2,5-diones, F, may be cleaved as described above.

EXAMPLE 6

Decoding Procedure

A bead is placed in a 1.3 mm diameter pyrex capillary with 2 μL of acetonitrile. Ceric ammonium nitrate solution (2 μL of a 0.1 M aq. solution) and hexane (3 μL) are added and the two-phase mixture centrifuged briefly. The tube is sealed and left at 35° C. for 16 hrs, then opened. The organic layer is removed by syringe and mixed with 1 μL of N,O-bis(trimethylsilyl)acetamide. The silated tag solution (1 μL) is analyzed by GC with electron capture (EC) detection.

The GC analysis is performed with a Hewlett Packard 5890 plus gas chromatograph. On column injection into a 5 m, 0.32 mm retention gap connected to a 25 m, 0.2 mm crosslinked 5% phenylmethyl silicone column is used. The temperature and pressure programs for the analysis are 200–320° C., 15° C./min, then 320° C. for 10 min and 20–40 psi at 2 psi/min, then 40 psi for 10 min. The EC detector is maintained at 400° C. and the auxiliary gas is set at 35 psi.

The identity of the library compound attached to the bead is ascertained based on the reagents utilized in the synthesis of such compound, which are readily determined from the binary codes associated, respectively, with each of the identifiers for such reagents, as characterized through the above procedure.

I claim:

1. A method of synthesizing a 1,4-benzodiazepin-2,5-dione which comprises:
   a. attaching an amino-protected α-aminoacid or an amino-protected N-alkyl α-aminoacid to a solid support via its carboxyl group to form a resin linked amino-protected α-aminoacid or amino-protected N-alkyl α-aminoacid;
   b. cleaving an amino protecting group from said resin linked amino-protected α-aminoacid or amino-protected N-alkyl α-aminoacid to provide a resin linked α-aminoacid or N-alkyl α-aminoacid;
   c. acylating said resin linked α-aminoacid or N-alkyl α-aminoacid with a 2-azidobenzoyl chloride to form a resin linked N-(2-azidobenzoyl)aminoacid; and
   d. cyclizing said resin linked N-(2-azidobenzoyl) aminoacid via aza-Wittig ring closure to provide a resin linked 1,4-benzodiazepin-2,5-dione.

2. A method according to claim 1 additionally comprising the step of cleaving said resin linked 1,4-benzodiazepin-2,5-dione from said resin to provide a 1,4-benzodiazepin-2,5-dione.

3. A method of synthesizing a 1,4-benzodiazepin-2,5-dione which comprises:
   a. attaching an amino-protected α-aminoacid to a solid support via its carboxyl group to form a resin linked amino-protected α-aminoacid;
   b. cleaving an amino protecting group from said resin linked amino-protected α-aminoacid to provide a resin linked α-aminoacid;
   c. reductively alkylating said linked α-aminoacid with an aldehyde and a reducing agent to provide a resin linked N-alkyl α-aminoacid;
   d. acylating said resin linked N-alkyl α-aminoacid with a 2-azidobenzoyl chloride to form a resin linked N-(2-azidobenzoyl)aminoacid; and
   e. cyclizing said resin linked N-(2-azidobenzoyl) aminoacid via aza-Wittig ring closure to provide a resin linked 1,4-benzodiazepin-2,5-dione.

4. A method according to claim 3 additionally comprising the step of cleaving said resin linked 1,4-benzodiazepin-2,5-dione from said resin to provide a 1,4-benzodiazepin-2,5-dione.

5. A method according to claim 1 which comprises:
   (a) reacting a suitably protected α-aminoacid of the formula:

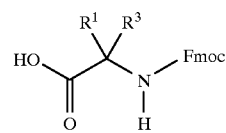

in the presence of DMF and DMAP with a solid support suspended in methylene chloride to form a resin linked N-protected aminoacid of the formula:

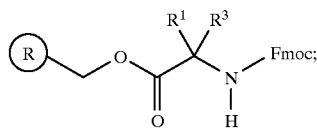

(b) cleaving the Fmoc from said resin linked N-protected aminoacid to provide a resin linked aminoacid;
   (c) reacting the resin linked aminoacid of step (b), suspended in DMF and acetic acid, with an aldehyde of the formula $HC(O)R^2$ in HOAc/DMF and sodium cyanoborohydride in THF to form a resin linked N-alkyl-α-aminoacid of the formula:

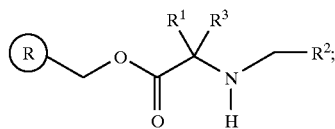

(d) reacting the resin linked N-alkyl-α-aminoacid of step (c), in methylene chloride and diisopropylethylamine, with a 2-azidobenzoyl chloride of formula:

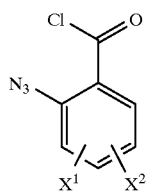

to form a resin linked N-(2-azidobenzoyl)amino ester of formula:

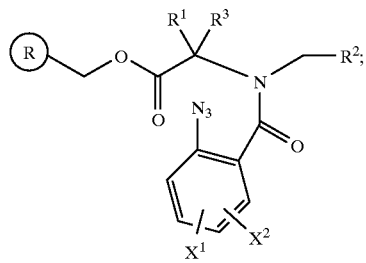

and (e) treating the resin linked N-(2-azidobenzoyl)amino ester of step (d), suspended in an involatile solvent, with an excess of a trivalent phosphorus reagent at 80–150° C. and then cooling said mixture to room temperature to form a resin linked benzodiazepine of formula:

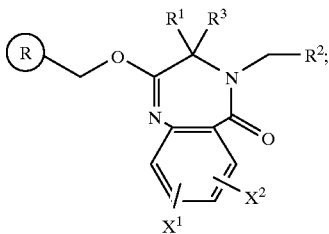

wherein:
R¹ is H, lower alkyl, c-lower alkyl, -or (CH₂)ₘR⁴, or R¹ and R², together with the atoms to which they are attached, join to form a 5-, or 6-membered heterocyclic ring, optionally monosubstituted with OH, alkoxy, or arylalkoxy;
R² is H, loweralkyl, arylR⁶R⁷R⁸, or heteroarylR⁶R⁷R⁸, or R¹ and R², together with the atoms to which they are attached, join to form a 5-, or 6-membered heterocyclic ring, optionally monosubstituted with OH, alkoxy, or arylalkoxy;
R³ is H or loweralkyl,
R⁴ is aryl, substituted aryl, heteroaryl, substituted heteroaryl, NR³R⁵, CO₂R³, CONR³R³, or OH;
R⁵ is H, lower alkyl, —C(=NR³)NHR³, or —C(O)R³;
R⁶,R⁷, and R⁸ is each, independently, H, lower alkyl, lower alkoxy, halogen, aryl, lower alkythio, X-aryl, X-substituted aryl, lower alkylaryl, C(hal)₃, —(CH₂)ₘNR³R⁵, or —X—CH(CO₂R³)₂, or R⁶ and R⁷, together with the atoms to which they are attached, join to form a 5- or 6-membered heterocyclic ring;
X is O or S;
X¹ and X² are independently chosen from hydrogen, loweralkyl, loweralkoxy, loweralkylthio, hydroxy, cyano, nitro, phenoxy, benzyloxy, halo, aryl, —NH(C=O)R³ and carboxy, or X¹ and X² taken together represent a fused benzene ring substituted with hydrogen, loweralkyl, loweralkoxy, loweralkylthio, hydroxy, cyano, nitro, phenoxy, benzyloxy, halo, aryl, —NH(C=O)R³ or carboxy; and

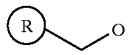

is a derivatized solid support.

6. A method according to claim 5 additionally comprising the step of:
(f) suspending the resin linked benzodiazepine of step (e) in TFA/water at room temperature for 1–24 hours to form a 1,4-benzodiazepin-2,5-dione of formula:

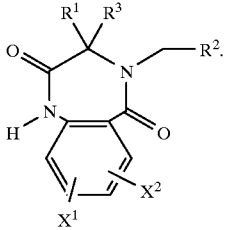

7. A method according to claim 5 herein the involatile solvent is toluene, xylene, or chlorobenzene and the trivalent phosphorus reagent is triphenylphosphine or tributylphosphine.

8. A method according to claim 1 which comprises:
(a) reacting a suitably protected α-aminoacid of the formula:

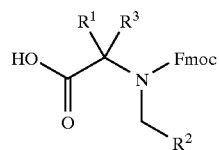

in the presence of DMF and DMAP with a solid support suspended in methylene chloride to form a resin linked aminoacid of the formula:

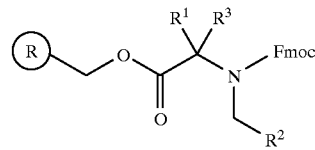

(b) cleaving the Fmoc from said resin linked N-protected aminoacid to provide a resin linked aminoacid;
(c) reacting the resin linked N-alkyl-α-aminoacid of step (b), in methylene chloride and diisopropylethylamine, with a 2-azidobenzoyl chloride of formula:

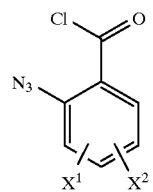

to form a resin linked N-(2-azidobenzoyl)amino ester of formula:

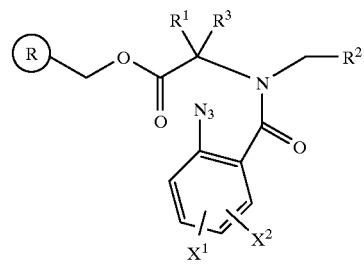

(d) treating the resin linked N-(2-azidobenzoyl)amino ester of step (c), suspended in an involatile solvent, with an excess of a trivalent phosphorus reagent at 80–150° C. and then cooling said mixture to room temperature to form a resin linked benzodiazepine of formula:

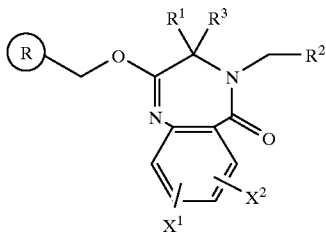

wherein:
R[1] is H, lower alkyl, c-lower alkyl, -or $(CH_2)_m R^4$, or $R^1$ and $R^2$, together with the atoms to which they are attached, join to form a 5-, or 6-membered heterocyclic ring, optionally monosubstituted with OH, alkoxy, or arylalkoxy;

R[2] is H, loweralkyl, aryl$R^6R^7R^8$, or heteroaryl$R^6R^7R^8$, or $R^1$ and $R^2$, together with the atoms to which they are attached, join to form a 5- or 6-membered heterocyclic ring, optionally monosubstituted with OH, alkoxy, or arylalkoxy;

R[3] is H or loweralkyl,

R[4] is aryl, substituted aryl, heteroaryl, substituted heteroaryl, $NR^3R^5$, $CO_2R^3$, $CONR^3R^3$, or OH;

R[5] is H, lower alkyl, —C(=NR$^3$)NHR$^3$, or —C(O)R$^3$;

R[6], R[7], and R[8] is each, independently, H, lower alkyl, lower alkoxy, halogen, aryl, lower alkylthio, X-aryl, X-substituted aryl, lower alkylaryl, C(hal)$_3$, —(CH$_2$)$_m$NR$^3$R$^5$, or —X—CH(CO$_2$R$^3$)$_2$, or R$^6$ and R$^7$, together with the atoms to which they are attached, join to form a 5- or 6-membered heterocyclic ring;

X is O or S;

X[1] and X[2] are independently chosen from hydrogen, loweralkyl, loweralkoxy, loweralkylthio, hydroxy, cyano, nitro, phenoxy, benzloxy, halo, aryl, —NH(C=O)R$^3$ and carboxy, or X$^1$ and X$^2$ taken together represent a fused benzene ring substituted with hydrogen, loweralkyl, loweralkoxy, loweralkylthio, hydroxy, cyano, nitro, phenoxy, benzyloxy, halo, aryl, —NH(C=O)R$^3$ or carboxy; and

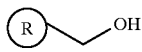

is a derivatized solid support.

9. A method according to claim 8 additionally comprising the step of:

(e) suspending the resin linked benzodiazepine of step (d) in TFA/water at room temperature for 1–24 hours to form a 1,4-benzodiazepin-2,5-dione of formula:

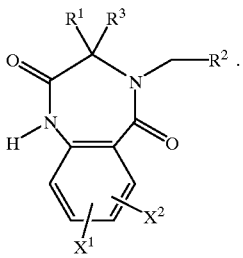

10. A method of claim 8 wherein the involatile solvent is toluene, xylene, or chlorobenzene and the trivalent phosphorus reagent is triphenylphosphine or tributylphosphine.

11. A method of synthesizing, 1,4-benzodiazepin-2,5-diones of the formulae:

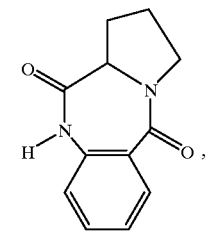

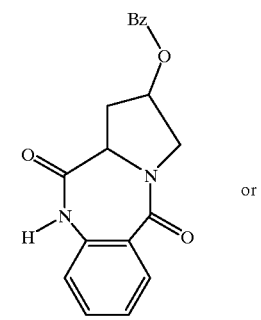

or

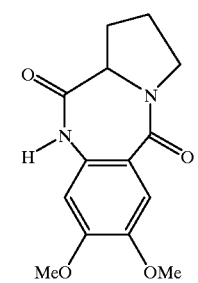

which comprises:

a) reacting a resin-linked α-amino ester of the formula:

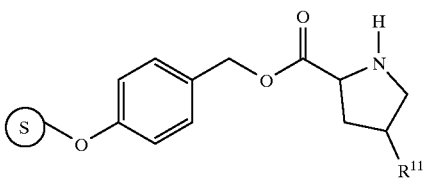

wherein

Ⓢ is a solid support and R[11] is hydrogen or benzyloxy, suspended in an aprotic, polar solvent and an excess of a soluble organic base with an excess of a substituted 2-azidobenzoyl chloride of the formula:

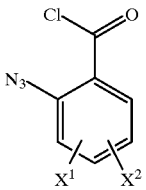

wherein X[1] and X[2] are hydrogen or methoxy, to produce a resin-linked N-(2-azidobenzoyl)amino ester;

b) suspending said resin-linked ester in an involatile solvent and treating said suspension with an excess of a trivalent phosphorus reagent at 80–140° C. for 2–24 hr. to produce a resin-linked 1,4-benzodiazepin-5-one of the formula:

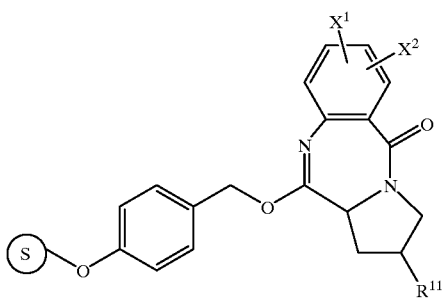

and c) suspending said resin-linked 1,4-benzodiazepin-5-one in an acidic solution at room temperature for 1–24 hr. to produce a 1,4-benzodiazepin-2,5-dione of the formula:

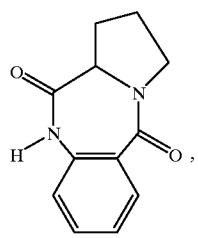

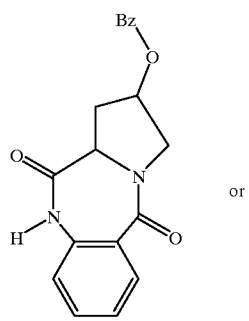

or

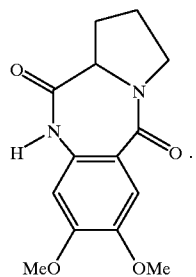

12. A method of synthesizing a 1,4-benzodiazepin-2,5-dione of the formula:

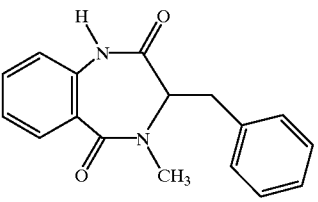

which comprises:

a) reacting a resin-linked α-amino ester of the formula:

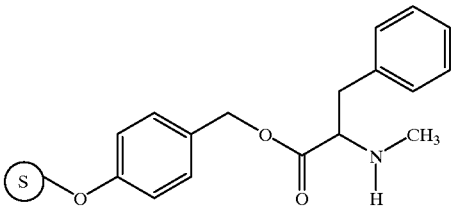

wherein

Ⓢ is a solid support, suspended in an aprotic, polar solvent and an excess of a soluble organic base with an excess of a substituted 2-azidobenzoyl chloride of the formula:

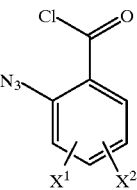

wherein $X^1$ and $X^2$ are hydrogen, to produce a resin-linked N-(2-azidobenzoyl)amino ester;

b) suspending said resin-linked ester in an involatile solvent and treating said suspension with an excess of a trivalent phosphorus reagent at 80–140° C. for 2–24 hr. to produce a resin-linked 1,4-benzodiazepin-5-one of the formula:

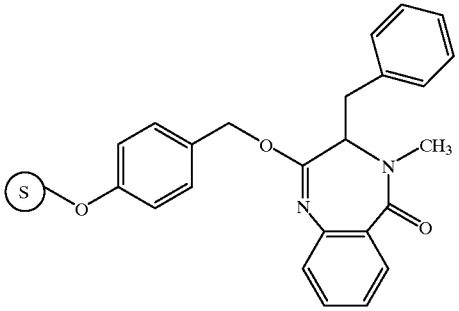

and
c) suspending said resin-linked 1,4-benzodiazepin-5-one in an acidic solution at room temperature for 1–24 hr. to produce a 1,4-benzodiazepin-2,5-dione of the formula:
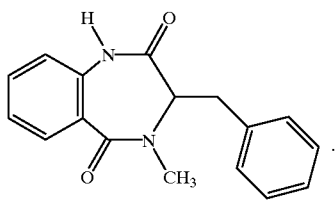
13. A compound of the formula:
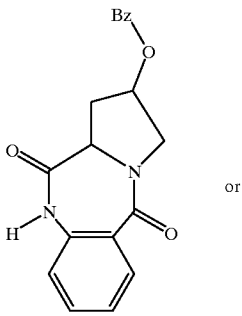
or
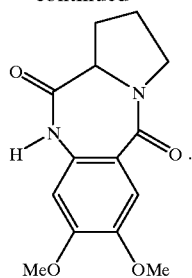
14. A compound of the formula:
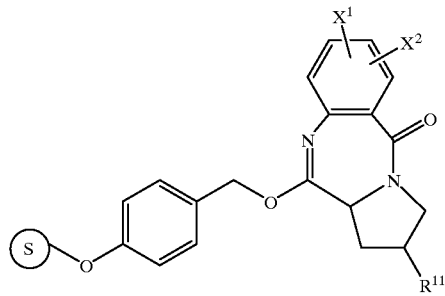
wherein
Ⓢ is a solid support;
$R^{11}$ is hydrogen or benzyloxy; and
$X^1$ and $X^2$ are hydrogen or methoxy.
* * * * *

UNITED STATES PATENT AND TRADEMARK OFFICE
CERTIFICATE OF CORRECTION

PATENT NO. : 5,962,337
DATED : October 05, 1999
INVENTOR(S) : Michael H.J. Ohlmeyer It is certified that error appears in the above-identified patent and that said Letters Patent is hereby corrected as shown below:

Col. 19, line 61, second structure under "PREPARATION 1", delete "H" and replace with --Fmoc--.

Signed and Sealed this

Fourth Day of April, 2000

Attest:

Attesting Officer

Q. TODD DICKINSON

Director of Patents and Trademarks